United States Patent [19]
Jann et al.

[11] Patent Number: 5,883,714
[45] Date of Patent: Mar. 16, 1999

[54] METHOD AND APPARATUS FOR DETECTING DEFECTS ON A DISK USING INTERFEROMETRIC ANALYSIS ON REFLECTED LIGHT

[75] Inventors: Peter C. Jann, Santa Clara; George A. Burt, Jr., Fremont; Joel Libove, Orinda, all of Calif.

[73] Assignee: Phase Metrics, San Diego, Calif.

[21] Appl. No.: 726,914

[22] Filed: Oct. 7, 1996

[51] Int. Cl.$^6$ .................................................. G01B 9/02
[52] U.S. Cl. .................... 356/349; 356/357; 356/359; 356/237.2
[58] Field of Search ..................... 356/237, 349, 356/351, 357, 359, 350; 250/559.16; 369/58

[56] References Cited

U.S. PATENT DOCUMENTS

| | | | |
|---|---|---|---|
| 4,794,264 | 12/1988 | Quackenbos et al. | . |
| 4,794,265 | 12/1988 | Quackenbos et al. | . |
| 4,832,487 | 5/1989 | Mikuriya et al. | 356/237 |
| 4,844,616 | 7/1989 | Kulkarni et al. | 356/237 |
| 5,371,588 | 12/1994 | Davis et al. | 356/349 |
| 5,504,571 | 4/1996 | Eckerman et al. | . |
| 5,661,559 | 8/1997 | Brezoczky et al. | 356/359 |

*Primary Examiner*—Samuel A. Turner
*Attorney, Agent, or Firm*—Blakely, Sokoloff, Taylor & Zafman

[57] ABSTRACT

A simple yet versatile non-contact optical inspection instrument and method are described for measuring the height and width of defects and contaminants on a magnetic disk surface. The instrument includes a sensor which produces an illumination beam that is modulated and then focused normally on the disk surface as a spot. The illumination spot is Doppler shifted due to the movement of the disk and the diffusely reflected light is interfered with a reference beam produced by the sensor's illumination optics. The sensor uses two collection optics channels which simultaneously detect both the specular reflected light and the diffuse scattered light produced by the disk surface. The phase shift of the specular reflected light and that of the diffusely scattered light are measured. The output signals from the sensors are processed to estimate the size and type of the defects. Another aspect of the present invention includes a demodulator which increases the frequency of an FM signal. Pulses representing the zero-crossings of the signal are generated and filtered to provide a voltage that is proportional to the frequency of the FM signal. Because the pulse train has a frequency that is significantly greater than the input frequency, a low-pass filter with both a high cut-off frequency and a gradual roll-off in frequency response may thus be used to optimize the output or demodulated signal in terms of increased bandwidth or faster response and more linear group delay.

24 Claims, 19 Drawing Sheets

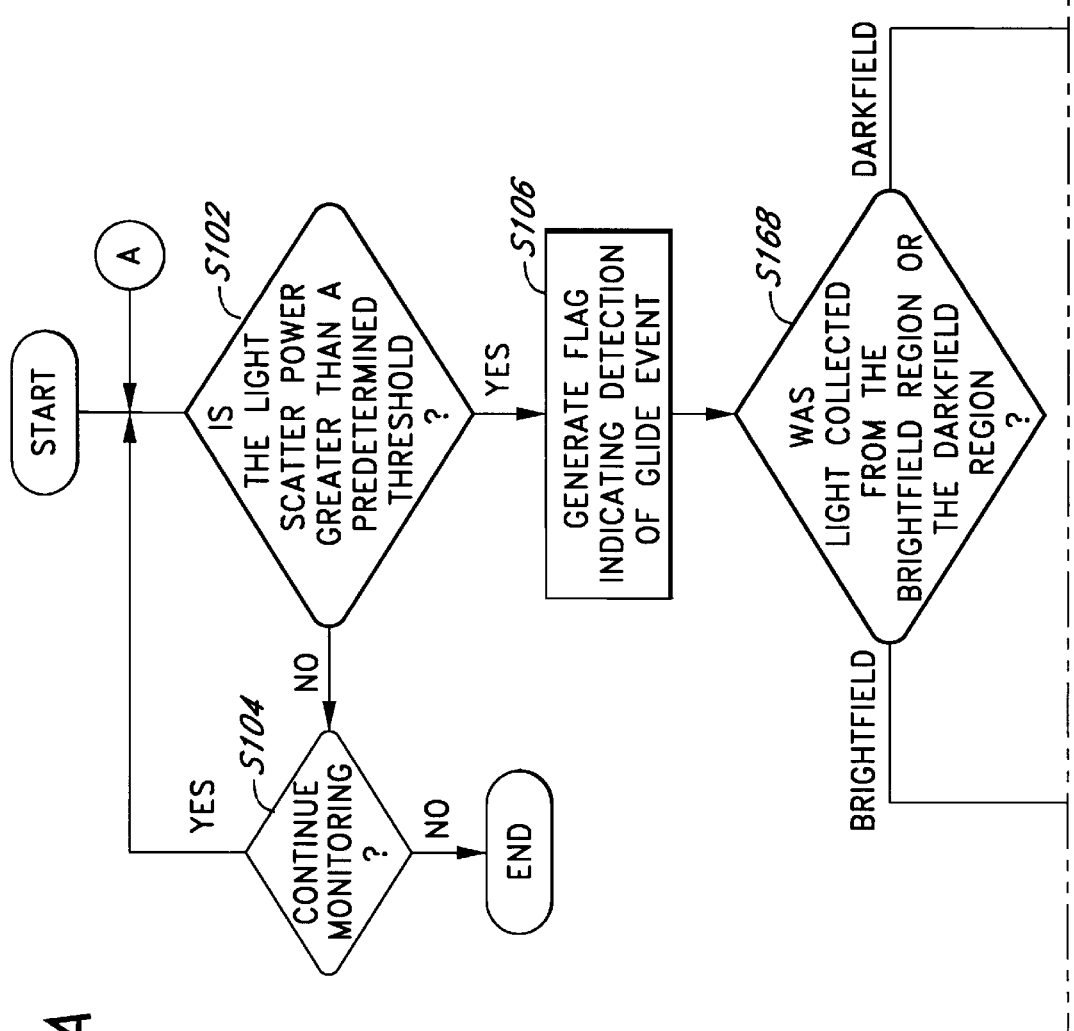

METHOD AND APPARATUS FOR DETECTING DEFECTS ON A DISK USING INTERFEROMETRIC ANALYSIS ON REFLECTED LIGHT

BACKGROUND OF THE INVENTION

1. Field of the Invention

The present invention relates to the field of defect detection in disk storage systems, and more particularly, to a method and apparatus for providing the profile of defects on the surface of a magnetic disk.

2. Description of the Related Art

There is a significant quality control problem associated with surface imperfections on magnetic disks. This typically occurs, for example, on nickel-plated aluminum substrates used in the manufacture of thin-film magnetic media, but may be a problem with respect to any area where a smooth surface is desired. Typical surface defects include pits, dirt, dust, oil, stains, fingerprints and the like. Defects on the surface of rigid magnetic media are often a result of an impingement onto the surface or a tearing of material away from the surface.

These types of defects can be very large scratches or gouges on the surface or very small (5 μm and smaller) tears or pricks on the surface. The large surface defects, because of their size and scattering properties, are readily distinguishable through sophisticated data processing performed on light reflected from the surface of the medium under test by an inspection apparatus which includes a light source directed at the disk. Small surface defects (5 μm and smaller) have not been so readily detectable, and even when detected, have been difficult to identify and classify.

For example, the systems described in U.S. Pat. Nos. 4,794,264 and 4,794,265, entitled "Surface Defect Detection And Confirmation System And Method" and "Surface Pit Detection System And Method", respectively issued to Quackenbos, describe systems for detecting pits on a smooth surface by irradiating an area of the surface. Two sensors separately detect radiation scattered from the surface. One sensor detects radiation scattered in a near-specular region (40–100 milliradians or 2.29–5.73 degrees), while a second sensor detects radiation scattered in a far-specular region (greater than 100 milliradians or 5.73 degrees). The near-specular signal is normalized with respect to the far-specular signal to indicate a pit. However, the '264 and '265 devices lack any means for distinguishing between a surface depression, i. e., a pit, and a surface protrusion, i. e., a bump. The '264 and '265 references also make the assumption that surface depressions or "pits" do not have far-specular reflection patterns, which has proved to be a limiting and problematic assumption. Moreover, the Quackenbos devices lack any means for determining the heights or depths of defects or contaminants, such as bumps, pits and scratches.

Another example of existing defect detection systems include brightfield interferometric systems. In such interferometric systems, light of a particular frequency is reflected off a disk and collected in the near-specular region. The reflected light is then interfered with a reference beam to produce an interference pattern. Although such brightfield interferometric systems can readily detect large surface defects, they cannot easily detect small surface defects. To increase the sensitivity of such brightfield interferometric systems, the size of the illumination spot which is focused on the surface must be decreased. More of the illuminating wavefront is therefore perturbed by the surface defect. This results in less throughput, due to a small diameter illumination spot, but also requires the use of a focus servo to keep the illumination spot in focus. Small illumination spots are formed with large numerical apertures which in turn produce little depth-of-focus.

Thus, there is a need in the magnetic disk drive industry for a non-contact optical inspection instrument which is capable of detecting and providing the profile of defects on the surfaces of polished magnetic disk substrates. This instrument must be sensitive, fast and inexpensive and must be capable of detecting surface defects and estimating the size of these defects. This instrument must also be able to distinguish between various kinds of defects such as bumps, pits and scratches and also between these defects and surface contaminants such as particles and stains. The instrument should also be able to determine the heights and depths of these contaminants or defects while simultaneously providing high sensitivity and throughput.

In optical systems, electro-optic modulators or acousto-optic modulators are typically used in establishing an optical communication link. The information signal is typically impressed electro-optically as an amplitude modulation on a laser beam. Alternatively, the information signal is impressed acousto-optically as a frequency modulation on the laser beam. The signal is subsequently recovered by an optical detector which includes a demodulator.

One common class of Frequency Modulation (FM) demodulators operates by detecting the zero-crossings of the input signal, providing a precise pulse at each zero crossing, and then low-pass filtering these pulses to obtain a voltage that is proportional to the frequency of the input signal. This method is suitable in situations where the modulation frequency is far lower than the carrier frequency, such as in commercial FM receivers, where the carrier frequency is typically 100 MHz and where the maximum frequency modulation or deviation is only about +/−30 KHz. However, if these conventional detectors are used in systems where the modulation frequency is rapidly changing, such as in interferometer systems, the response of the low-pass filter must be very steep. This is necessary to accommodate the high modulation frequency while blocking the undesirable signal energy at the zero-crossing frequency. In addition to being costly, such steep low-pass filters exhibit undesirable phase and group delay variations in the pass-band, making them unsuitable for many applications. For example, in imaging applications, in which rapidly changing spatial surface characteristics are detected as rapidly varying electrical frequency, such group delay variations will cause small objects or sharp edges in large objects to appear to be slightly displaced in position, causing an aberration on the resulting image.

Accordingly, there is a need in the technology for a demodulator which can accommodate high modulation frequencies while blocking undesirable signal energy at the zero-crossing frequency of the modulated signal. The demodulator must also exhibit minimal phase and group delay variations in the pass-band.

BRIEF SUMMARY OF THE INVENTION

A simple yet versatile non-contact optical inspection instrument and method are described for measuring the height and width of defects and contaminants on a magnetic disk surface. The instrument includes a sensor which produces an illumination beam that is modulated and then focused normally on the disk surface as a spot. The illumination spot is Doppler shifted due to the movement of the disk and the diffusely reflected light is interfered with a reference beam produced by the sensor's illumination optics. The sensor uses two collection optics channels which simultaneously detect both the specular reflected light and the diffuse scattered light produced by the disk surface. The phase shift of the specular reflected light and that of the diffusely scattered light are measured. The output signals from the sensors are processed to estimate the size and type of the defects. Another aspect of the present invention includes a demodulator which increases the frequency of an FM signal. Pulses representing the zero-crossings of the signal are generated and filtered to provide a voltage that is proportional to the frequency of the FM signal. Because the pulse train has a frequency that is significantly greater than the input frequency, a low-pass filter with both a high cut-off frequency and a gradual roll-off in frequency response may thus be used to optimize the output or demodulated signal in terms of increased bandwidth or faster response and more linear group delay.

DETAILED DESCRIPTION OF THE PREFERRED EMBODIMENT

A surface inspection apparatus and method is described. In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

Figure 1:
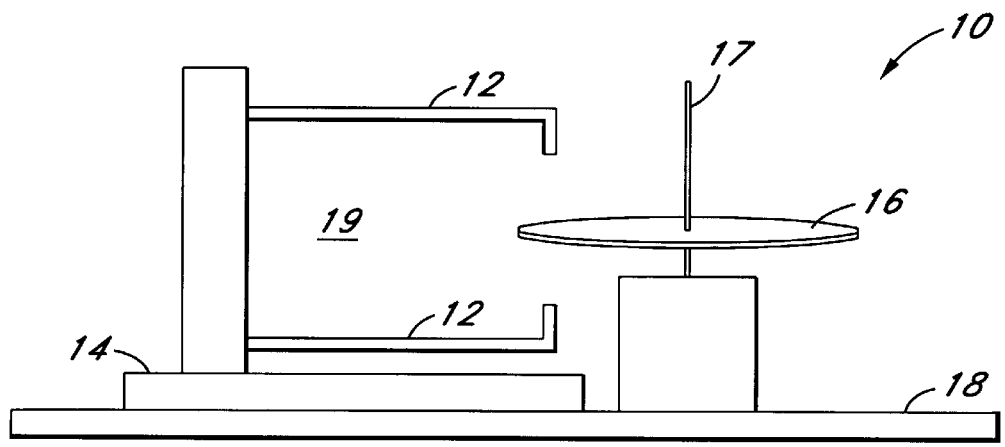
FIG. 1 illustrates a system for inspecting disk surfaces in accordance with the teachings of the present invention.

As shown in FIG. 1, the surface inspection apparatus of the present invention, generally illustrated at 10, comprises dual sensors 12 mounted on a carriage 14 and situated in relation to a magnetic disk substrate 16 such that one sensor monitors a first surface of the disk 16 while the other sensor monitors of a second surface of the disk 16. The magnetic disk substrate 16 is rotated about an axis 17 during operation of the inspection apparatus. The carriage 14 is preferably movable along a track 18 so that the inspection apparatus of the present invention can be used to produce a scan of an entire disk as the carriage 14 is translated along the radius of the disk 16 as it is rotated. Each of the sensors 12 is capable of distinguishing bumps, pits and scratches from surface contamination and quantitatively characterizing the geometry of the former while providing information regarding their location on the medium being examined.

The magnetic disk substrate which is being inspected may be held by a vacuum chuck and rotated by an air bearing spindle. Two diametrically opposed non-contact optical sensors may be simultaneously radially translated over each of the disk surfaces by the carriage, thereby producing spiral shaped inspection scans of both surfaces of the disk. These scans consist of adjacent tracks which may or may not overlap depending upon the throughput and precision required of the tool.

Figure 2:
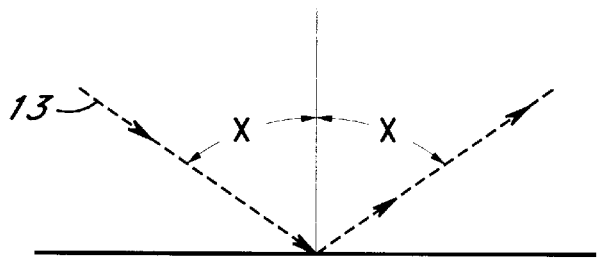
FIG. 2 illustrates specular reflection from a smooth surface employed by the present invention to sense the slope and magnitude of a defect on a disk under examination.

The physical principles employed by the present invention to sense defects in the disk 16 under examination are shown schematically in FIGS. 2 and 3. The sensors 12 use two forms of light reflected from the disk 16 to characterize defects. The first form of reflected light is specularly reflected from smooth regions of the disk, as illustrated in FIG. 2. The sensor 12 shines an incident beam of light 13 at the disk 16 under examination. The light beam 13 is preferably incident at a normal or near-normal angle to the plane of the disk 16. If the surface of the disk 16 has a defect which imparts a local non-zero slope to the disk, the beam 13 will be reflected specularly according to the law of reflection at an angle X equal to the angle the beam 13 makes with the extended local normal surface 15 of the disk.

Figure 3A:
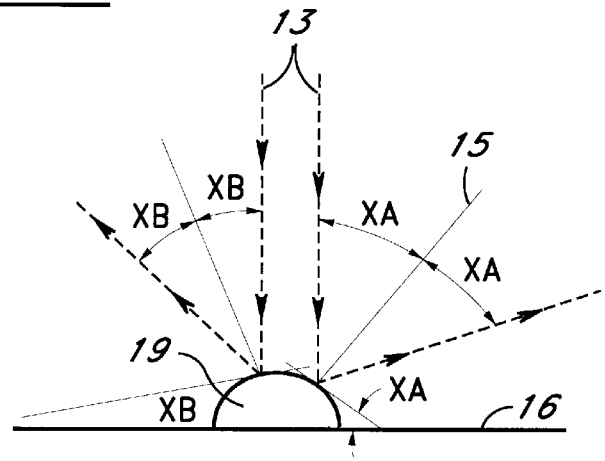
FIGS. 3A and 3B illustrate the geometrical principles of diffuse reflection of an incident light beam from a surface.
Figure 3B:
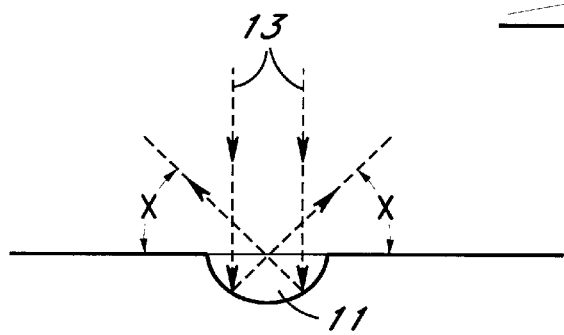

The sensor 12 also uses diffusely-reflected light to sense particles and other small defects which scatter incident light from the surface of the disk. In FIGS. 3A and 3B, the incident beam 13 is incident on a region of the disk 16 which contains a small defect 19 or pit 11. The small defect 19 or pit 11 scatters the incident light in many directions simultaneously. This diffusely-scattered light is detected by the sensor 12 to characterize defects which do not specularly reflect incident light, such as dirt particles or other small irregularities on the surface of the disk 16. The sensor 12 is illustrated in more detail in FIG. 5.

One aspect of the present invention involves a defect inspection apparatus and method for detecting reflected or scattered light whose field amplitude distribution's frequency is Doppler shifted in proportion to the velocity of the asperity or glide event on the disk surface. To detect the occurrence of either a pit or a bump on the disk, an acousto-optic modulator is used to impart an 80 MHz constant amplitude carrier signal on the illumination beam's field amplitude distribution. Interference of the illumination and reference beams is detected and simple numerical integration techniques are used with the frequency demodulated signals to yield event height distributions which can then be threshold detected to estimate event height, width and polarity. The field amplitude distribution of either the illumination or reference beam must have the 80 MHz constant amplitude carrier if heterodyne detection is to be achieved. A smooth disk surface will therefore produce an 80 MHz signal without a Doppler frequency shift, while a pit will produce a signal with a Doppler shifted positive frequency less than 80 MHz and a bump will produce a signal with a Doppler shifted positive frequency greater than 80 MHz. These positive frequency signals can be successfully frequency demodulated, as will be described later, to give both the magnitude and sign of the asperity's velocity distribution. Pits can therefore be distinguished from bumps. Homodyne detection, on the other hand, does not use a constant amplitude carrier in either the illumination or reference beams. A smooth disk surface will therefore produce a zero frequency signal without a Doppler shift, while a pit will produce a signal with a Doppler shifted negative frequency less than 0 Hz and a bump will produce a signal with a Doppler shifted positive frequency greater than 0 Hz. Upon demodulation, however, both the positive and negative frequency shifts are handled the same way and the sign information is lost. Therefore, pits cannot be distinguished from bumps using homodyne detection; only the magnitude of the asperity's velocity distribution can be obtained.

Extremely small surface defects and surface contaminants on the disk 16 such as particles, scatter the incident light in many directions. The scattered light or wavefront contains phase information which directly describes the defect's height distribution, as described in detail in the following sections. However, when the defect is much smaller than the illumination spot, only a very small portion of the perturbed wavefront is contained within the specularly reflected beam or brightfield channel. Thus, the phase of only a very small percentage of the light power collected by this brightfield channel is affected by the defect. On the other hand, virtually all of the light which is collected by the darkfield channel is produced by defect scatter. The darkfield channel is only illuminated when small defects pass through the illumination spot and virtually all of this illumination (although it comprises a small percentage of illumination spot power), contains phase information which directly describes the defect. Interferometric techniques are utilized in the present invention to collect light reflected off asperities on a disk in the darkfield region so as to obtain the profile of the asperities.

Figure 4:
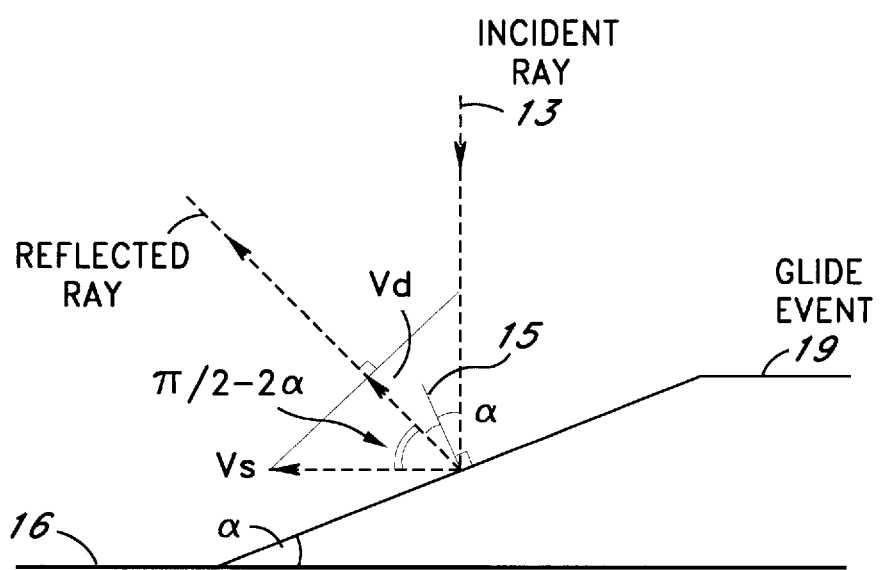
FIG. 4 illustrates the geometrical principles involved in obtaining the velocity of a glide event located on a surface.

With reference to FIG. 4, when the incident beam 13 is focused as an illumination spot upon the disk surface 16, the disk's surface complex reflectance distribution will induce a Doppler shift upon the illumination spot's complex field amplitude distribution. Upon reflection, these two distributions are convolved and the phase term in the disk's surface complex reflectance distribution is added to the phase term of the complex field amplitude distribution of the illumination spot. The Doppler velocity may be calculated as follows:

Assuming that $v_a$ is the disk angular velocity in rev/min and r is the radius in mm. The disk surface velocity $v_s$ may be obtained using the following expression:

$$v_s = \frac{2*1000*\pi*r*v_a}{60} \; \mu\text{m/s}$$

The Doppler velocity $v_d$ of the asperity on the disk may be obtained using the following expression:

$$v_d = v_s \cos\left[\frac{\pi}{2} - 2\alpha\right] \mu\text{m/s}$$

where $\alpha = \frac{\arcsin(NA)}{2}$, and

NA=numerical aperture of the illumination spot.

The Doppler velocity $v_d$ may be differentiated over time to obtain acceleration. Based on the surface acceleration, the force imparted to a magnetic head flying above the disk may be computed. In addition, the Doppler velocity $v_d$ may be integrated over time to obtain the height of the asperity, thus providing a profile of the defect or contaminant as a function of time.

Figure 5:
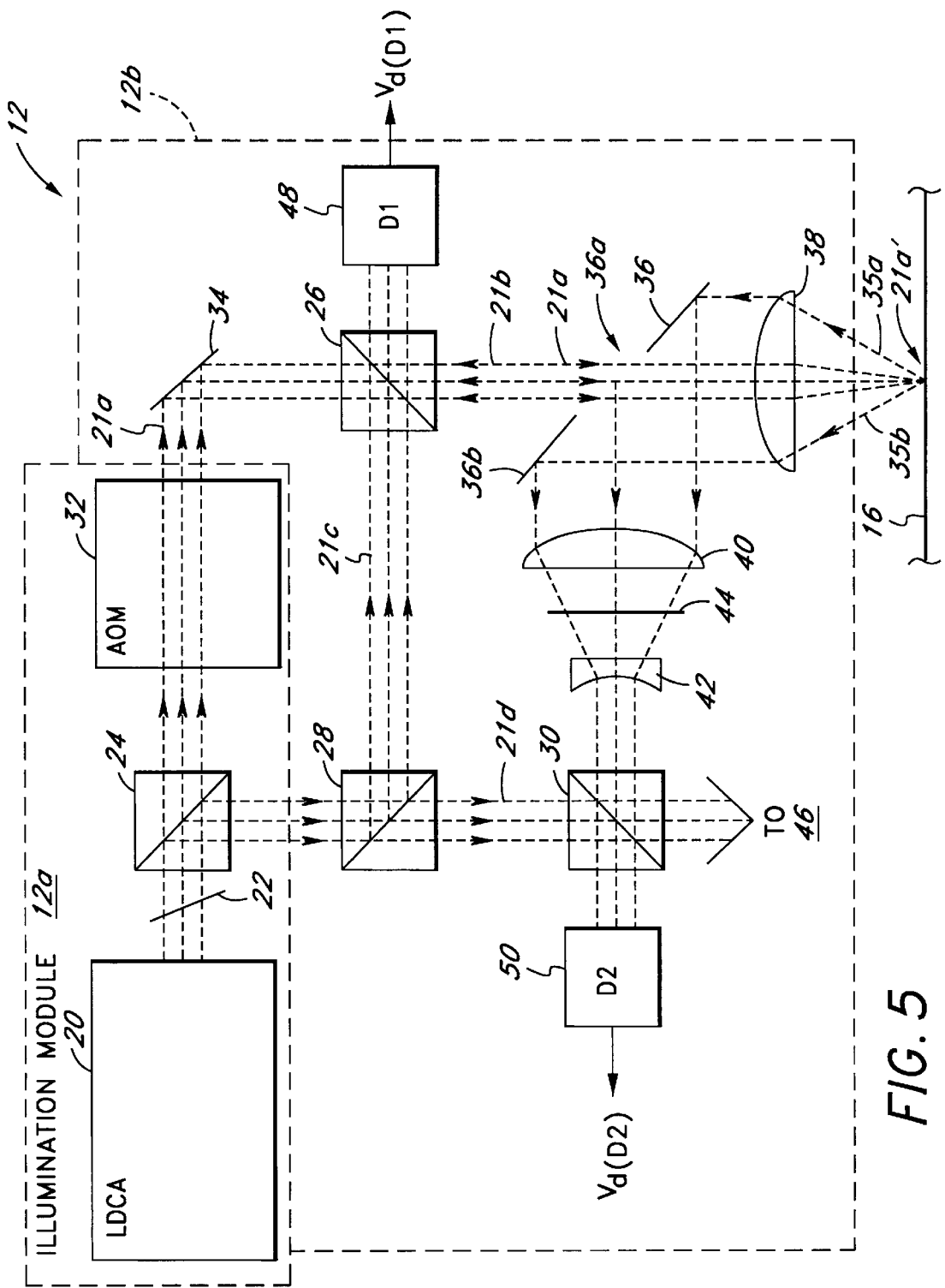
FIG. 5 is a schematic illustration of a first embodiment of the disk inspection system of the present invention.

Reference is now made to FIG. 5. Since the two sensors 12 shown in FIG. 1 are substantially the same, only one will be shown from hereon to avoid unnecessary duplication. It is to be understood that two or more sensors may be employed. The sensor 12 includes a sensor illumination module 12a and a sensor interferometer module 12b. The illumination module 12a includes a laser diode collimator assembly (LDCA) 20, a quarter wave plate 22, a first 50/50 beamsplitter 24, and an acousto-optic modulator 32. The sensor interferometer module 12d includes a second 50/50 beamsplitter 26, a third 50/50 beamsplitter 28, a fourth 50/50 beamsplitter 30, a mirror 34, a mirror with a center hole 36, first a plano-convex lens 38, a second plano-convex lens 40, a plano-concave lens 42, a spatial filter in the form of an opaque slit 44, a beam dump 46, a first detector 48 and a second detector 50.

The sensor assembly 12 operates as follows. The collimated output beam 21 of the LDCA 20 has a field amplitude distribution with a nominal frequency $f_0$, and propagates along an optical path which includes: the quarter wave plate 22, the first beamsplitter 24, the acousto-optic modulator 32 which modulates the collimated output beam's 21 field amplitude distribution with a constant amplitude carrier of frequency $f_1$, the mirror 34, the second beamsplitter 26, the mirror with a center hole 36, and the first piano-convex lens 38. The carrier beam 21a is brought to a focus on the surface of the magnetic disk surface 16 to form an illumination spot 52. Typically, the disk illumination spot 52 is about 15 $\mu$m in diameter, has a numerical aperture of 0.03, is circularly polarized, has a wavelength of 670 nm and is normally incident upon the surface of the disk 16. The small numerical aperture precludes the need for a focus servo subsystem to accommodate any disk axial run-out, while the laser diode collimator assembly 20 includes an output power servo circuit to stabilize the assembly's output.

As the surface of the magnetic disk surface 16 moves through the focused illumination spot 52, two kinds of reflected light are produced from the disk surface 16, as described above. The first kind of light is a specularly reflected beam 21b which is circularly polarized and propagates along an optical path which includes: the first plano-convex lens 38, the opening 36a in the mirror with a hole 36, the second beamsplitter 26 and the first detector 48. The first detector 48 also receives light from a reference beam 21c which originates from the LDCA 20 and which travels along an optical path which includes: the quarter wave plate 22, the first beamsplitter 24, a third beamsplitter 28, the second beamsplitter 26 and the first detector 48.

The field of the reference beam 21c may be represented as follows:

$$E_r(x, y, t) = A_r(x, y)e^{-i2\pi f_0 t} \quad (1)$$

where $A_r$ is the amplitude of the reference beam 21c;

$f_0$ is the frequency of the reference beam 21c; and t is time.

The field of the specularly reflected beam 21b can be represented as follows:

$$E_s(x, y, t) = A_s(x, y)e^{-i2\pi(f_0 + f_1 + \delta f(t))t} \quad (2)$$

where $A_s$ is the amplitude of the specularly reflected beam 21b;

$f_0$ is the frequency of the reference beam 21c;

$f_1$ is the frequency of the carrier beam 21a;

$\delta f(t)$ is the change in frequency; and t is time.

In a preferred embodiment, $f_1$ is either 40 MHz or 80 MHz.

When the carrier beam 21a is focused as an illumination spot 21a' upon the disk 16, the disk's 16 surface complex reflectance distribution will induce a Doppler shift upon the illumination spot's 21a' complex field amplitude distribution. Upon reflection, these two distributions (i.e., the disk's 16 surface complex reflectance distribution and the illumination spot's 21a' complex field amplitude distribution) are convolved and the phase term in the disk's 16 surface complex reflectance distribution is added to the phase term of the complex field amplitude distribution of the illumination spot 21a'. The reflected illumination beam 21b is interfered with the reference beam 21c on the surface of detector 48 and the intensity of the resulting light is detected by the detector 48. In response, the detector 48 generates an output current which is proportional to the incident light power which is fluctuating with a 40 or 80 MHz carrier which is Doppler frequency modulated or shifted.

The second kind of reflected light which is produced by the disk surface is a diffuse, highly divergent, diffracted or scattered beam 35 which is elliptically polarized and is collected by the piano-convex lens 38. The piano-convex lens 38 refracts this light onto the mirror portion 36b of the mirror with hole 36, which in turn reflects the light towards the second plan-convex lens 40. In response, the second plano-convex lens 40 directs the light towards the opaque slit 44, which subsequently directs the light towards the plano-concave lens 42. The piano-concave lens 42 directs the light in parallel rays towards beamsplitter 30, which provides the light to the second detector 50. The field of the scattered beam 35 is also of the form represented as in equation (2).

The second detector 50 also receives light from a reference beam 21d which travels along an optical path which includes: the LDCA 20, the quarter wave plate 22, the first beamsplitter 24, the third beamsplitter 28, the fourth beamsplitter 30 and the second detector 50. The field of the reference beam 21d is of the form as represented in equation (1).

As in the case of the specularly reflected light, when the modulated carrier beam 21a is focused as an illumination spot 21a' upon the disk 16, the disk's 16 surface complex reflectance distribution will induce a Doppler shift upon the illumination spot's complex field amplitude distribution. Upon reflection, these two distributions are effectively multiplied and the phase term in the disk's 16 surface complex reflectance distribution is added to the phase term of the complex field amplitude distribution of the illumination spot. The specularly reflected light beam 35 is interfered with the reference beam 21d on the surface of the detector 50. The intensity of the resulting light is detected by the detector 50. The detector 50 subsequently generates an output current which is proportional to the incident light power which is fluctuating with a 40 or 80 MHz carrier which is Doppler frequency modulated or shifted.

Since the outputs of the first detector 48 and that of the second detector 50 may be processed in the same manner, as discussed in detail below, only the second detector 50 will be referred to in discussing the signal processing aspects of the present invention. In one embodiment, the second detector 50 drives transconductance amplifiers which provide voltage waveforms which vary sinusoidally with time. The instantaneous frequency of these waveforms will depend upon the Doppler shift induced by the disk's 16 surface complex reflectance distribution upon the illumination spot's complex field amplitude distribution, as discussed earlier. Upon reflection, these two distributions are multiplied and the phase term in the surface complex reflectance distribution is added to the phase term of the complex field amplitude distribution of the illumination spot. The incident intensity at D2 is of the form:

$$I_d(x,y,t) = [E_r(x,y,t) + E_s(x,y,t)][E_r^*(x,y,t) + E_s^*(x,y,t)]$$
$$= I_r(x,y) + I_s(x,y) + 2[I_r(x,y)I_s(x,y)]^{1/2}\cos[2\pi(f_1 + \delta f(t))t]$$

Upon interference with the reference beam 21c and subsequent detection of the intensity at the second detector D2, the phase term from the surface of the disk 16 phase modulates the carrier beam 21a from the AOM 32. This modulation or change in frequency is readily observed in the detector output signal $V_{d(D1)}$ or $V_{d(D2)}$ (for discussion purposes, $V_d$ represents either $V_{d(D1)}$ or $V_{d(D2)}$) and is represented by:

$$\delta f(t) = \frac{2\cos(I)v(t)}{\lambda}$$

where $\delta f(t)$ is the Doppler frequency shift;

I is the illumination angle of incidence;

v(t) is the axial velocity normal to the surface of the disk 16; and $\lambda$ is the illumination wavelength.

The output voltage of the detector 50 is of the form represented as follows:

$$V_d(t) = R_1 \int_0^T \left[ \int\int_{A_d} I_d(x,y,t')R_d(x,y)dxdy \right] h_d(t - t')dt' \quad (3)$$

where $R_1$ is the detector load resistor value;

$A_d$ is the detector area;

$R_d(x, y)$ is the detector response distribution in Amp/Watt;

$h_d(t)$ is the detector impulse response function;

T is integration interval over time t' and t is the convolution shift variable

Upon integration of the right hand portion of equation (3) over $A_d$ and T, the following expression is obtained:

$$V_d(t) = V_{ave} + V_{amp}\cos[2\pi(f_1 + 2v(t)/\lambda)t] \qquad (4)$$

where $V_{ave}$ is the average voltage; and

Vamp is the amplitude of the ac component of $V_d$.

The output voltage $V_d$ of each detector 48 or 50 is then provided to a signal processing system, as discussed below, to demodulate the output voltage in frequency to obtain surface velocity versus time. The instantaneous surface velocity may be differentiated over time to obtain acceleration. Based on the surface acceleration obtained, the force imparted to a magnetic head flying above a disk surface may be estimated. In addition, the output instantaneous surface velocity may be integrated to obtain surface height versus time or profiles of surface defects on the magnetic disk.

Figure 6:
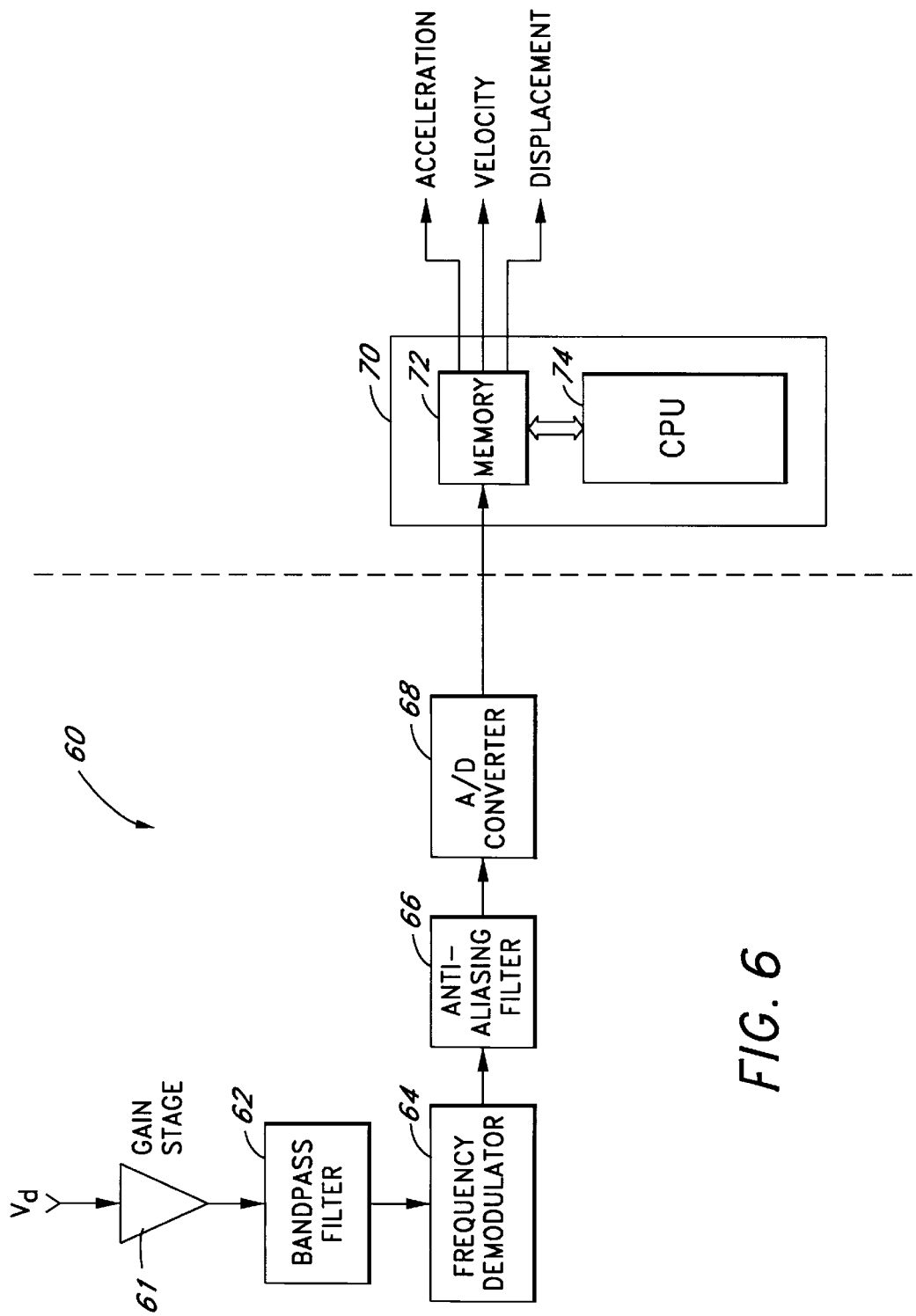
FIG. 6 is a schematic of a signal processing technique used to detect and classify defects of the present invention.

Referring now to FIG. 6, a system level block diagram of the signal processing aspects of the present invention is shown. The signal processing system 60 is used for processing the output signals of the detectors 48 and/or 50. Light from the reference beam 21*c* and reflections 21*b* from the rotating disk 16 generate an interference pattern which is imaged onto the detector 48 or 50. The intensity distribution resulting from the interference pattern from the two beams 21*c* and 21*b* are analyzed by the signal processing system 60 of FIG. 6. The detector 48 or 50 produces an output current indicative of the intensity of the light incident on the individual surface of the first detector 48 or the second detector 50. For present purposes only one detector 48 will be referred to, although the signal processing system 60 may be used to process signals detected by either detector 48 or 50.

The detector 48 produces a signal current corresponding to the intensity or power of the light received associated with the specular or brightfield channel. The signal current is provided to a pre-amplifier 61 where it is converted to voltage and then amplified. The amplified signal is provided to a bandpass filter 62, which filters the signal and subsequently provides the filtered signal to a frequency demodulator 64. The output of the frequency demodulator 64 is provided to an anti-aliasing filter 66, the function of which is to low pass filter the signal to prevent undersampling or aliasing when the signal is sampled by the analog-to-digital (A/D) converter. The output of the filter 66 is then provided to an A/D converter 68 which digitizes the filtered signal. The digitized signal is then sent to a computer 70 for processing. The digitized signal may be stored in a register or memory 72 located within the computer 70, which is accessible by a central processing unit (CPU) 74, also located within the computer 70. The digitized signal is then either numerically integrated to give the asperity's height distribution or differentiated to give the asperity's acceleration distribution.

Figure 7A:
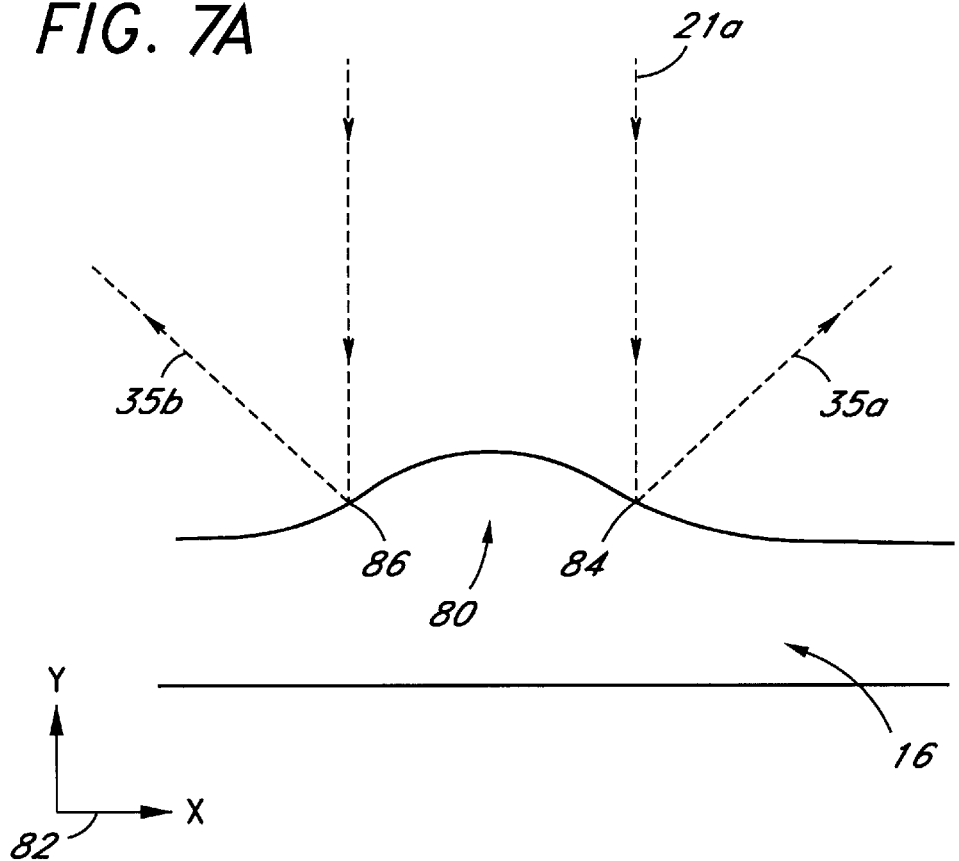
FIG. 7A illustrates the principles of the Doppler effect when an incident light beam is reflected off an asperity located on a rotating surface.

FIG. 7A illustrates the principles of the Doppler effect when an incident light beam is reflected off an asperity 80 located on the rotating disk 16, in the nonspecular region. For discussion purposes, the disk 16 is rotating in an anti-clockwise direction 82. When the illumination beam 21*a* is focused on the disk 16, portions of the illumination beam 21*a* striking the asperity 80 on a descending slope 84 of the disk 16 will be reflected along the direction of rotation 82, as reflected beam 35*a*. Portions of the illumination beam 21*a* striking the asperity 80 on an ascending slope 86 of the asperity 80 will be reflected along a direction opposite to the direction of rotation 82, as reflected beam 35*b*. As is known in the technology, when a light source is moving relative to an observer, there is a shift in the observed frequency. For present discussion purposes, the light source is reflected beam 35 (which includes forward scattered light 35*a* and back scattered light 35*b*), and the observer is located at lens 38. Since the disk is rotating in an anti-clockwise direction 82, the observed frequency of the reflected beam 35*a* will be different from that of its actual frequency, as well as that of the reflected beam 35*b*.

The following sections provide a discussion of the frequency shift or light scattered from a moving object, where the source and observer are stationary relative to each other. This may be considered as a double Doppler shift from source to moving object and then from object to the observer. A more complete discussion on this topic is provided in Section 3.4 of *The Laser Doppler Technique* by L. E. Drain.

Figure 7B:
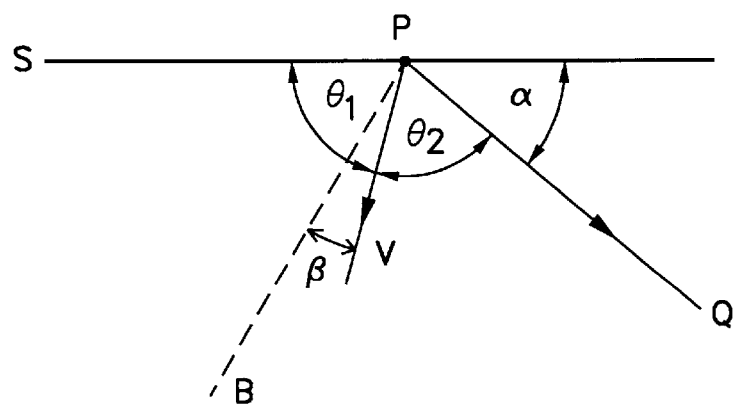
FIG. 7B illustrates the principles of the Doppler effect when light of frequency $f$ from a source S is scattered by an object P.

In FIG. 7B we consider light of frequency $f$ from a source S scattered by the object P, the scattered light being observed at Q. The angles that the direction of motion make with PS and PQ are denoted by $\theta_1$ and $\theta_2$. The frequency $f'$ observed by P is given by equation (5).

$$f' = \frac{f}{\sqrt{(1 - v^2/c^2)}} \left(1 + \frac{v}{c}\cos\theta_1\right) \qquad (5)$$

where c is the speed of light; and v is the velocity of a moving object.

Light of this frequency is re-emitted by P and received by Q as $f''$ where $$f'' = \frac{f'\sqrt{(1 - v^2/c^2)}}{1 - (v/c)\cos\theta_2} \qquad (6)$$

as is known by one skilled in the technology. Thus, $$\frac{f''}{f} = \frac{1 + (v/c)\cos\theta_1}{1 - (v/c)\cos\theta_2} \qquad (7)$$

For velocities small compared with c, which almost always is the case, equation (7) may be expanded to first order in V/C Thus, $$\Delta f = f'' - f = \frac{fv}{c}(\cos\theta_1 + \cos\theta_2) \qquad (8)$$

Applying a well-known trigonometrical transformation, we obtain $$\Delta f = \frac{2fv}{c}\cos\frac{\theta_1 + \theta_2}{2}\cos\frac{\theta_1 - \eta_2}{2} \qquad (9)$$

It will be seen from FIG. 7B that $$\alpha = \pi - (\theta_1 + \theta_2) \qquad (10)$$

where $\alpha$ is the angle of scattering and thus $$\sin\frac{\alpha}{2} = \cos\frac{\theta_1 + \theta_2}{2} \qquad (11)$$

In addition, $$\frac{\theta_1 - \theta_2}{2} = \beta \qquad (12)$$

where $\beta$ is the angle between the velocity vector and PB, the bisector of the angle between PS and PQ. PB is the direction of the scattering vector, a concept useful in the theory of scattering. It represents the momentum change of the radiation on scattering.

Thus, substituting equations (11) and (12) into equation (13), we obtain:

$$\frac{\Delta f}{f} = \frac{2v}{c} \cos \beta \sin \frac{\alpha}{2} \qquad (13)$$

Thus, the Doppler shift depends on the sine of half the angle of scattering and on $v \cos \beta$ which is the component of $v$ resolved in the direction of the scattering vector. Equation (13) may also be written in terms of the wavelength $\lambda$ (which is the name for the shifted and unshifted light to this approximation):

$$\Delta f = \frac{2v}{\lambda} \cos \beta \sin \frac{\alpha}{2} \qquad (14)$$

This is the most useful form of the Doppler shift equation.

When the source is receding from the observer, the observer measures a lower frequency. Conversely, when the source is approaching the observer, the observer measures a higher frequency. Thus, the forward scattered light 35a has a frequency which is higher than that of the back scattered light 35b.

The effect of a positive Doppler frequency shift, where a larger frequency is observed, and that of a negative Doppler frequency shift, where a smaller frequency is observed, are also encountered when light is reflected in the non-specular region. To accurately measure the forward scattered light 35a and the back scattered light 35b, the present invention provides additional interferometric elements and techniques, as discussed below.

Figure 8:
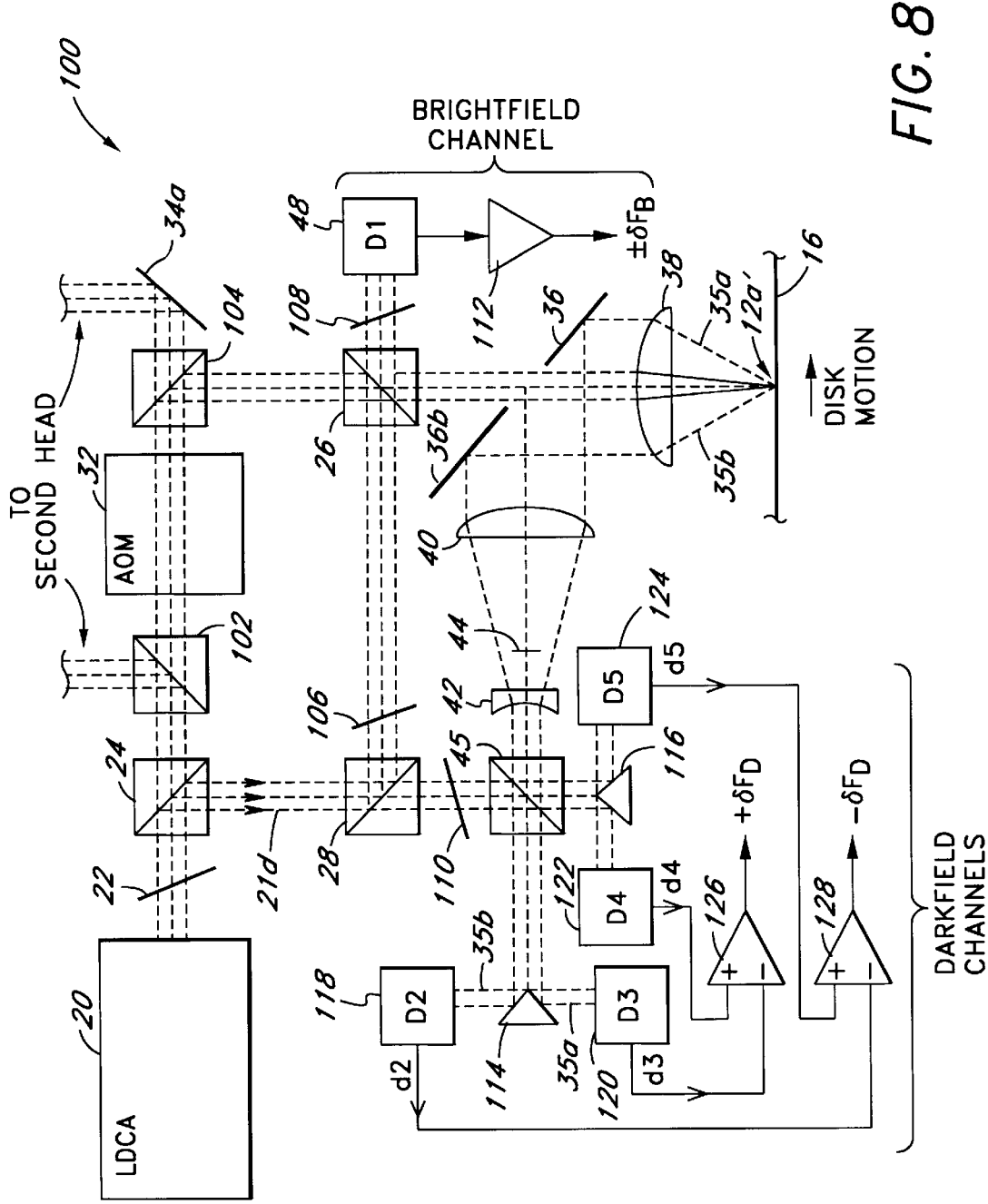
FIG. 8 is a schematic illustration of a second embodiment of the disk inspection system of the present invention.

An alternate embodiment of the present invention is illustrated in FIG. 8. In this embodiment, the specular channel of the sensor 100 is the same as that of the first embodiment described above. However, in this embodiment, additional interferometric elements and techniques are used in the darkfield channel to sense the forward and backward Doppler shifts in the scattered light, thereby allowing extremely accurate measurement of defects on the surface of the disk 16. In addition, additional interferometric elements and differential amplifiers are utilized to provide outputs with increased signal-to-noise ratios.

In the embodiment of FIG. 8, additional beamsplitters 102 and 104 are positioned adjacent to the AOM 32 to provide the illumination beam 21a to a second head (not shown) used in sensing defects on the disk 16. The use of the additional beamsplitters 102 and 104 facilitate increased throughput in the multi-channel heterodyne interferometer.

The elements utilized in the sensor 52 of FIG. 8 are identical to the sensor 12 of FIG. 5, with the exception that the darkfield channel utilizes four detectors, D2–D5, instead of the one detector (D2) 50 shown in FIG. 5. In addition, the detector (D1) 48 generates a signal that is first provided to a preamplifier 112 before being processed by the signal processing system of FIG. 6. The output $\pm \delta F_B$ of the preamplifier 112 is proportional to the intensity of the interference between the specularly reflected brightfield beam coming from the disk 16 and the reference beam 21d coming from beamsplitter 28. This output signal is positive Doppler frequency shifted if the surface of disk 16 is moving towards plano-convex lens 38 and negative Doppler frequency shifted if the disk surface is moving away from the lens.

As discussed earlier, the diffuse, highly divergent, diffracted or scattered beam 35 includes a forward scattered light beam 35a and a backscattered light beam 35b. The forward scattered light beam 35a and the back scattered light beam 35b are respectively collected by the plano-convex lens 38 and refracted onto the mirror portion 36b of the mirror with hole 36. The mirror portion 36b in turn reflects the forward scattered light beam 35a and the back scattered light beam 35b toward the second plano-convex lens 40. In response, the second plano-convex lens 40 directs the forward scattered light 35a and the back scattered light 35b toward the plano-concave lens 42. The plano-concave lens 42 directs the light beams 35a and 35b as parallel rays toward beamsplitter 45. The opaque slit 44 is used to block the light which is scattered or diffracted by any texture patterns which may be present on the surface of disk 16.

The right angled prism 114 directs the forward scattered light beam 35a towards detector 120 and also directs the back scattered light beam 35b towards detector 118. The beamsplitter 28 provides the reference beam 21d which is split by prism 114 and is therefore made to interfere with beams 35a and 35b on detectors 120 and 118, respectively. The detectors 118 and 120 generate output signals d2 and d3, respectively, corresponding to the intensity of the incident interference patterns and respectively provide the signals d2 and d3, to the inverting terminals of differential preamplifiers 128 and 126, respectively.

The beamsplitter 45 also directs the forward scattered light 35a and the back scattered light 35b towards detectors 122 and 124, respectively. Beamsplitter 28 likewise provides reference beam 21d which is split by prism 116 and is therefore made to interfere with beams 35a and 35b on detectors 122 and 124, respectively. The output signals d4 and d5 generated by detectors 122 and 124, respectively, which are proportional to the intensity of the corresponding interference patterns incident upon the detectors, are subsequently provided to the noninverting terminals of differential preamplifiers 126 and 128, respectively.

Differential amplifier 126 generates an output $+\partial F_D$ based on the output signals d4 and d3 provided from detectors 122 and 120. The difference between the output signals d4 and d3 received from detector 122 and detector 120 is that the interference pattern AC components in the output signals d4 and d3 are 180° out of phase. The net effect of the AC component phase difference of 180 degrees in combination with subsequent signal differencing or subtraction by the differential amplifier is to give an output signal with double the AC component amplitude; there is virtually no DC component from either: (1) the reference beams by themselves when there is no disk 16 surface asperity light scatter; or (2) the average level of the interference pattern's intensity distribution; and a reduction or cancellation in correlated noise from sources common to both of the differential preamplifier's inputs results. A larger signal-to-noise ratio may be obtained with this approach if the noise sources are correlated. Finally, a usefully signal will only be present at the differential amplifier's output when an asperity on the surface of disk 16 scatters light into this darkfield channel.

In particular, the output $+\partial F_D$ of differential amplifier 126 is the difference between the signals d4 and d3. Since the signals d4 and d3 are 180° out of phase, the output $+\partial F_D$ will be zero until light is reflected off an asperity, in which case a non-zero signal $+\partial F_D$ representative of the velocity of forward scattered light 35a collected in the darkfield region will be generated. An illustration of the output of differential amplifier 126 is shown in FIG. 9B.

Likewise, differential amplifier 128 generates an output, $-\partial F$, based on the output signals d5 and d2 provided from detectors 124 and 118 respectively. Again, the difference between the output signals d5 and d2 received from the detectors 124 and 118 respectively is that the output signals d5 and d2 are 180° out of phase. The output signal $-\partial F_D$ of differential amplifier 128 is the difference between the signals d5 and d2. Since these signals d5 and d2 are 180° out of phase, the output signal $-\partial F_D$ will be zero until light is reflected off an asperity, in which case a non-zero signal $-\partial F_D$, representative of the velocity of back scattered light collected in the darkfield region will be generated. An illustration of the output of differential amplifier 128 is shown in FIG. 9C.

Figure 9A:
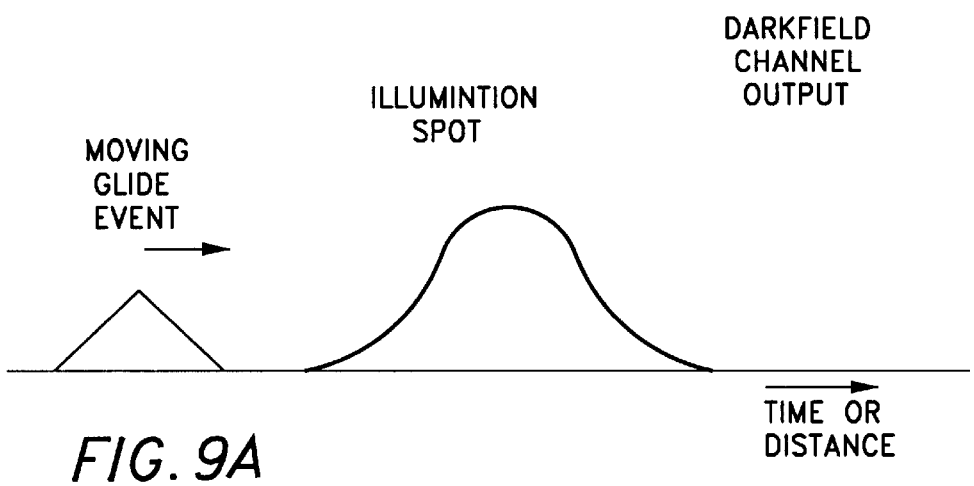
FIG. 9A illustrates the profile of a moving glide event 80 as shown in FIG. 7 and the profile of the illumination spot 21a' as shown in FIG. 9.
Figure 9B:
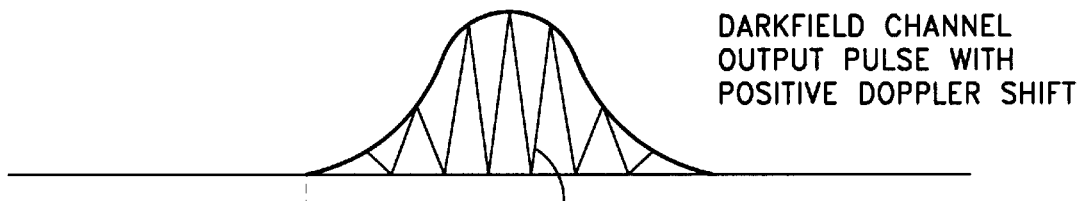
FIG. 9B illustrates the forward darkfield output signal $+\partial F_D$ of FIG. 8.
Figure 9C:
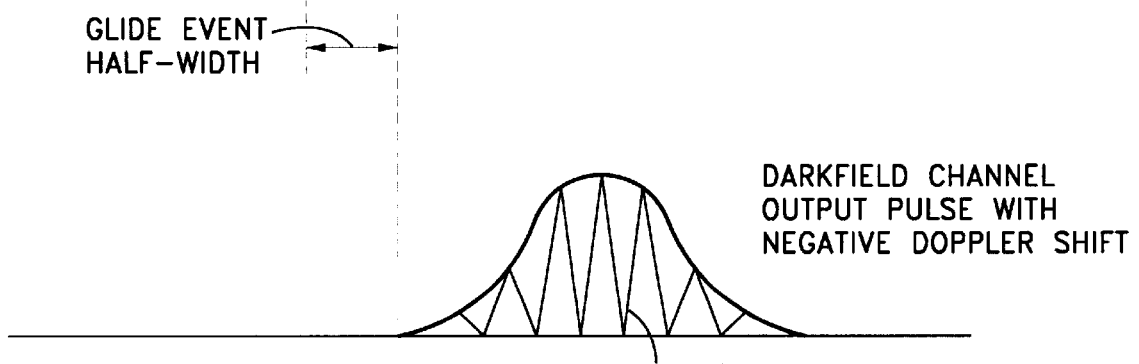
FIG. 9C illustrates the backward darkfield output signal $-\partial F_D$ of FIG. 8.

FIG. 9A illustrates the profile of a moving glide event 80 as shown in FIG. 7 and the profile of the illumination spot 21a' as shown in FIG. 9. FIGS. 9B and 9C illustrate the output signals $+\partial F_D$ and $-\partial F_D$, of FIG. 8, respectively. In particular, FIG. 9A illustrates an asperity or glide event 80 moving towards a Gaussian-shaped illumination spot 21a'. FIG. 9B illustrates the darkfield channel output signal $+\partial F_D$ with a positive Doppler shift as generated by differential amplifier 126 of FIG. 8. FIG. 9C illustrates the darkfield channel output signal $-\partial F_D$ with a negative Doppler shift as generated by differential amplifier 128 of FIG. 8. As shown, the signal $-\partial F$ generated by differential amplifier 128 is delayed by a half-width of the glide event 80 as compared to the signal $+\partial F_D$. The outputs $+\partial F_D$ and $-\partial F_D$ of differential amplifiers 126 and 128 respectively, may be processed to provide the height and width of the asperity off of which the forward scattered light and the back scattered light is reflected, as discussed in detail below.

Figure 10B:
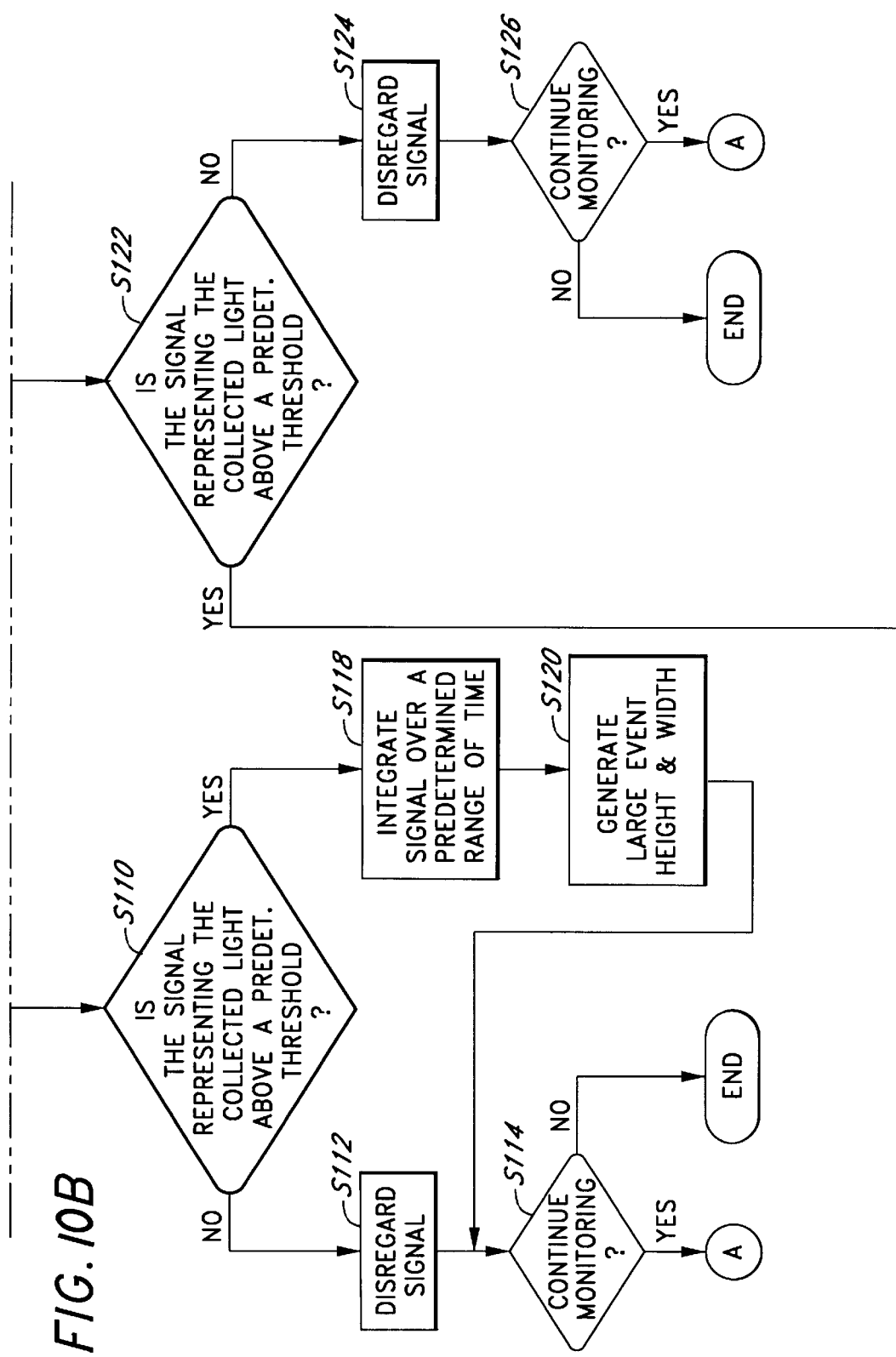
FIG. 10 (which includes FIGS. 10A–10C) is a flowchart of the signal processing method used in processing the brightfield output signal $\pm\partial F_B$ and darkfield output signals $+\partial F_D$ and $-\partial F_D$.
Figure 10C:
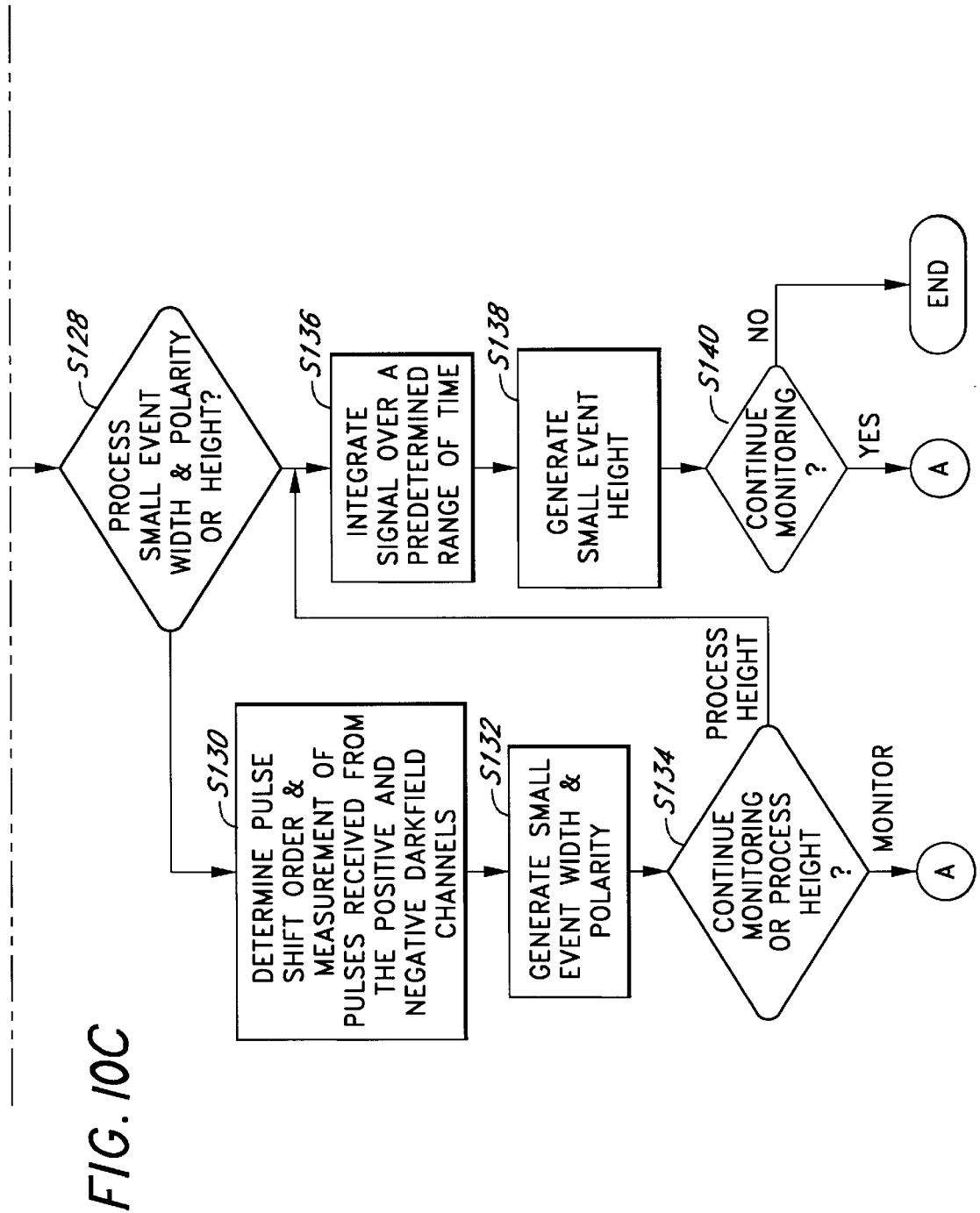

FIG. 10 is a flowchart of the signal processing method S100 used in processing the brightfield output signal $\partial F_B$ and darkfield output signals $+\partial F_D$ and $-\partial F_D$. The process S100 may be conducted within computer 70 of FIG. 6. As discussed earlier, the interferometer module 12d of the present invention detects reflected or scattered light whose field amplitude distribution's frequency is Doppler shifted in proportion to the velocity of the asperity or glide event on the disk surface. Simple numerical integration techniques are used with the frequency demodulated signals (obtained using the signal processing system 60 of FIG. 6) to yield glide event height distributions which can then be threshold detected to estimate event height, width and polarity.

The process S100 begins from a start state and proceeds to decision step S102, where it determines if the light scatter power is greater than a predetermined threshold. If the input signal voltage representing light scatter power is less than the predetermined threshold, the process S100 proceeds to decision step S104, where it queries if it should continue monitoring for defects. If so, the process returns to decision step S102. If not, the process S100 terminates.

If the light scatter power is greater than the predetermined threshold, the process S100 generates a flag indicating the detection of a glide event, as shown in process step S106. The process S100 then proceeds to process step S108, where it determines if the reflected light was collected from the brightfield region or the darkfield region. If the reflected light was collected from the brightfield region, the process S100 proceeds to decision step S110, where it determines if the signal representing the reflected light collected is above a predetermined threshold. In a preferred embodiment, the signal is indicative of the velocity of the asperity. If the signal not above the threshold, the process S100 disregards the signal (step S112) and proceeds to decision step S114, where it determines if it should continue monitoring for defects. If not, the process S100 terminates. Otherwise, the process S100 returns to decision step S102.

If it is determined at decision step S110, that the signal is above a predetermined threshold, the process S100 proceeds to process step S118, where it integrates the signal over a predetermined range of time. This predetermined range can be selected as desired. Based on the integrated signal, the process S100 calculates the height and width of the glide event. Since the signal is representative of light collected in the brightfield region, the integrated value of the signal is also indicative of the height and width of a large glide event. The process S100 then advances to decision step S114. This is because large glide events typically reflect light in the brightfield region.

If, at decision step S108, the process S100 determines that the reflected light was collected in the darkfield region, the process S100 proceeds to decision step S122, where it determines if the signals $+\partial F_D$ and $-\partial F_D$ representing the forward scattered light and the backscattered light are above their respective predetermined thresholds. If not, the process S100 disregards the signals (step S124) and proceeds to determine if it should continue monitoring for defects, as shown in process step S126. If it is determined that it should discontinue monitoring the process S100 terminates. If it is determined that it should continue monitoring, the process S100 returns to decision step S102.

If, at decision step S122, the process S100 determines that the signals $+\partial F_D$ and $-\partial F_D$ are above their respective predetermined thresholds, it proceeds to decision step S128, where it queries if it should process the width and polarity of the glide event or process the height of the glide event instead. Since the signals $+\partial F_D$ and $-\partial F_D$ are collected from the darkfield region, the glide event thus detected will be a small event, as small glide events scatter light diffusely. If it is determined that the width and polarity of the glide event is to be processed, the process S100 proceeds to process step S130, where it determines the pulse shift order of the signals $+\partial F_D$ and $-\partial F_D$ received from differential amplifiers 126 and 128 respectively. In particular, the relative timing or shift between the output signal pulses $+\partial F_D$ and $-\partial F_D$ provided from the two darkfield channels will be measured via threshold detection to determine the duration of the shift and to determine which burst occurs first. The shift duration will be used to estimate the width of the asperity and the burst order or sequence will be used to determine whether the event is a bump or a pit. If the burst with the positive Doppler shift occurs first, the event is a bump. If the burst with the negative Doppler shift occurs first, the event is a pit.

The process S100 then proceeds to decision step S134, where it queries if it should continue monitoring defects or if it should process the small event height. If it is determined that it should continue monitoring for defects, the process S100 returns to process step S102. Otherwise, it proceeds to process step S136. In addition, if, at decision step S128 it is determined that the small event height should be provided, the process S100 proceeds directly to process step S136.

At process step S136, the process S100 integrates each signal $+\partial F_D$ and $-\partial F_D$ over a predetermined range of time. Based on the integrated signals, the process S100 generates the small event height (S148). The process S100 then proceeds to decision step S150, where it queries it should continue monitoring for defects. If so, the process S100 proceeds to process step S102. If not, the process S100 terminates.

Figure 11:
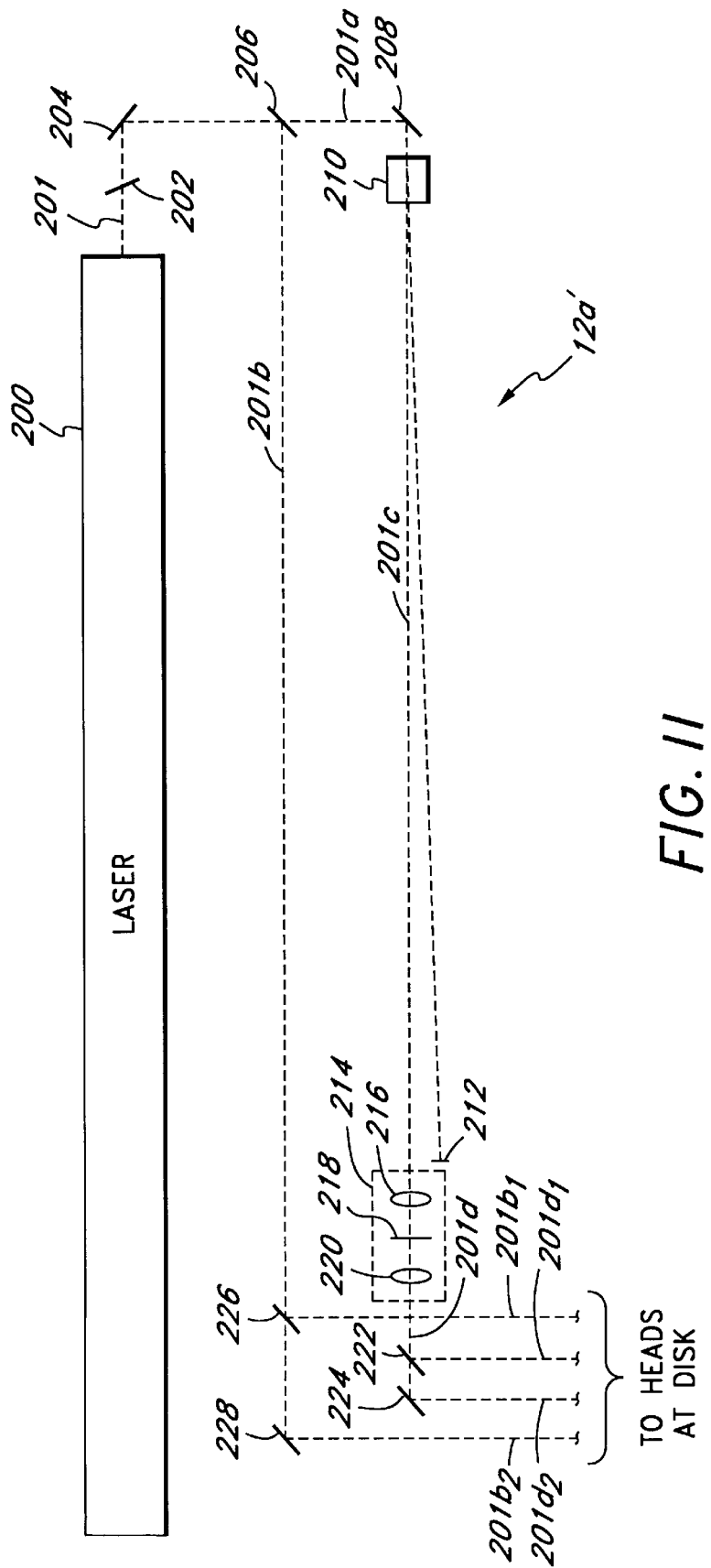
FIG. 11 illustrates another embodiment of the sensor illumination module 12a as shown in FIG. 5.

FIG. 11 illustrates an alternate embodiment 12a' of the illumination module 12a as shown in FIG. 5. The illumination module 12a' provides an illumination beam 201 from the laser 200, which travels along the following path: a quarter wave plate 202, a first flat mirror 204, a first 50/50 beamsplitter 206 which splits the illumination beam 201 into an illumination beam 201a and a reference beam 201b. The illumination beam 201a is reflected by a second flat mirror towards an acousto-optic modulator (AOM) 210, which modulates the illumination beam 201b into a carrier beam 201c which now has an 80 MHz constant amplitude carrier present in its field amplitude distribution. A zero-order stop 212 is located downstream from the AOM 210 to capture the nonmodulated output beam coming from the AOM 210. An alternate embodiment could use this output beam as the reference beam in place of the illustrated reference beam 201b.

The modulated carrier beam 201c is directed towards a 1× telescope/spatial filter 214 which filters the modulated carrier beam 201c before it is used as a focused spot on the disk surface 240. In one embodiment, the telescope/spatial filter 214 comprises a first achromat lens 216, a pinhole 218 and a second achromat lens 220. The filtered, modulated carrier beam 201d is provided to a second 50/50 beamsplitter 222, which splits the beam 201d into a first beam 201d1 (which is directed towards a first head located on the disk) and a second beam 201d2. The second beam 201d2 is directed towards a mirror 224, which reflects it towards a second head located on the disk.

The reference beam 201b is directed towards a third 50/50 beamsplitter 226, which splits the reference beam 201b into a first reference beam 201b1 (that is directed towards a first head located on the disk), and a second reference beam 201b2 which is directed towards a mirror 228, which subsequently directs the beam 201b2 towards a second head on the disk.

Figure 12A:
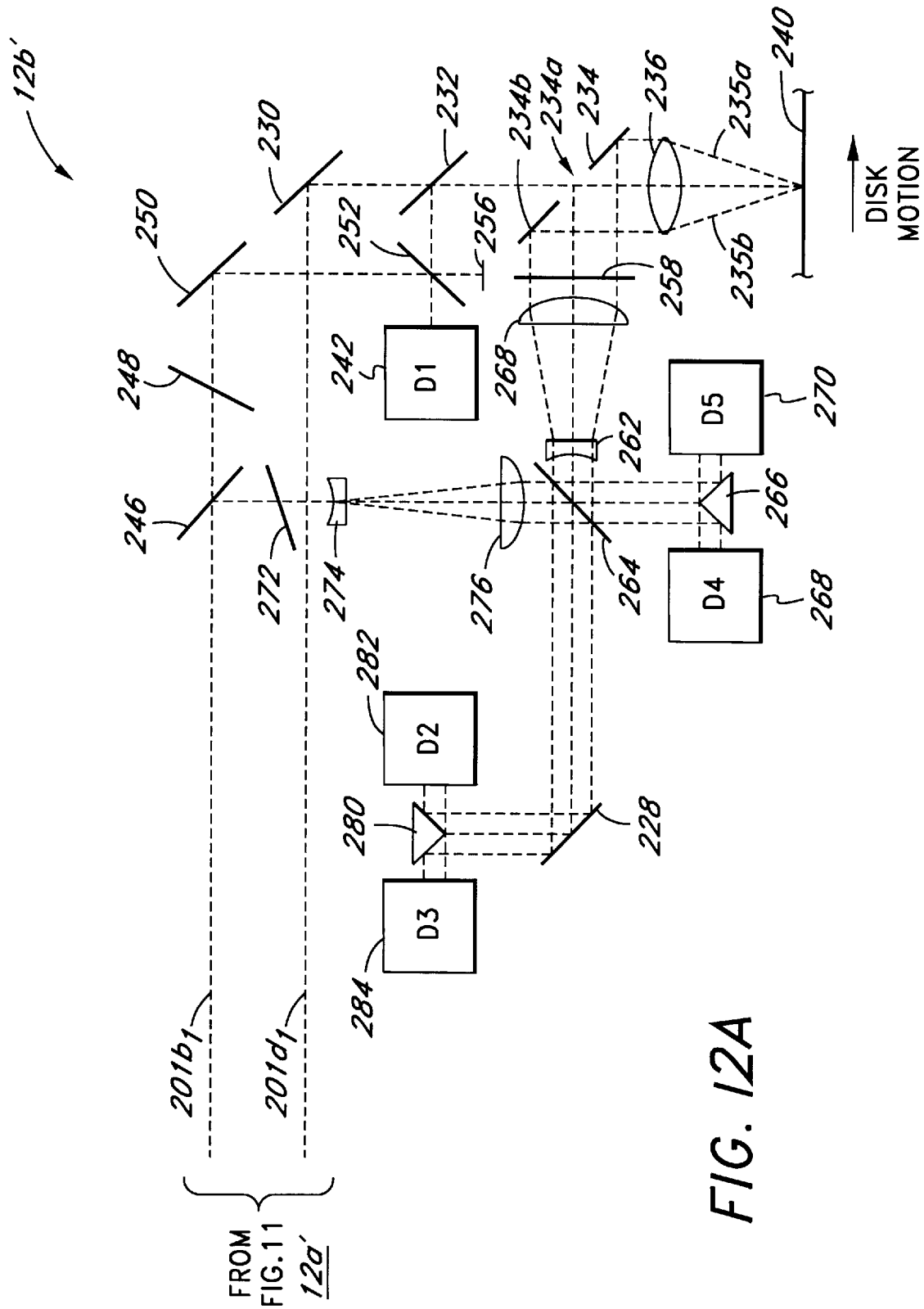
FIG. 12A illustrates another embodiment of the sensor interferometer module 12b as shown in FIG. 5.

FIG. 12A illustrates a further alternate embodiment of the sensor interferometer module 12b as shown in FIG. 5. The sensor interferometer module 12b' is similar to the sensor interferometer module 12b of FIG. 5 with the exception that two telescopes (each comprising a plano-concave lens and a plano-convex lens) are used instead of one (such as the plano-convex lens 40 and plano-concave lens 42 of FIG. 5). The use of two telescopes allow the diameters of the carrier and reference beams to be equalized where they combine and interfere with each other.

In particular, the sensor interferometer module 12b' receives the carrier beam 201d1 and the reference beam 201b1 from the illumination module 12a as shown in FIG. 11. The carrier beam 201d1 is directed towards a flat mirror 230 which reflects the beam 201d1 towards a 50/50 beamsplitter 232. The beamsplitter 232 directs the beam 201d1 through a mirror with a hole 234 and an achromat lens 236. The beam 201d1 is then focused as an illumination spot on the disk 240. Upon reflection off the disk 240, the beam 201d1 passes through the hole 234a of the mirror 234, and is directed by the beamsplitter 232 towards the detector 242.

The reference beam 201b1 is directed towards a 50/50 beamsplitter 246, which directs a portion of the reference beam 201b1 through a filter 248 and towards a mirror 250. The mirror 250 directs beam 201b1 to another 50/50 beamsplitter 252, which directs a portion of the beam 201b1 to the detector 242. The remaining portion of the beam 201b1 is collected by a beam dump 256.

The forward scattered light beam 235a and the back scattered light beam 235b are respectively collected by the achromat lens 236 and refracted onto the mirror portion 234b of the mirror with hole 234. The mirror portion 234b in turn reflects the forward scattered light beam 235a and the back scattered light beam 235b through a spatial filter 258 toward a plano-convex lens 268. The plano-concave lens 262 directs the light beams 235a and 235b as parallel rays toward a beamsplitter 264 and thereafter, to a right-angled prism 266.

The right angled prism 266 directs the forward scattered light beam 235a towards detector 268 and also directs the back scattered light beam 325b towards detector 270. The beamsplitter 264 also receives light from the reference beam 201b1 that travels along an optical path which includes: the beamsplitter 246, filter 272, the plano-concave lens 274, and the piano-convex lens 276. The beamsplitter 264 directs the reference beam 201b1 towards the detectors 268 and 270 via prism 266. Light from the reference beam 201b1 and the forward scattered light 235a generate an interference pattern which is formed on the detector 268. Similarly, light from the reference beam 201b1 and the backscattered light beam 235b form an interference pattern on the detector 270. The detectors 268 and 270 each generate a signal corresponding to the intensity distribution resulting from the interference pattern of the light received. Processing of the signals may proceed as described earlier.

The beamsplitter 264 also directs the forward scattered light 235a and the back scattered light 235b towards a mirror 228 and a right-angled prism 280, which provides the forward scattered light 235a to detector 282 and the backscattered light 235b to detector 284. Light from the reference beam 201b1 and the forward scattered light 235a form an interference pattern on the detector 282. Likewise, light from the reference beam 201b1 and the back scattered light 235b form an interference pattern on the detector 284. The detectors 282 and 284 each generate a signal corresponding to the intensity distribution resulting from the interference pattern of the light received. Processing of the signals may proceed as described earlier.

Figure 12B:
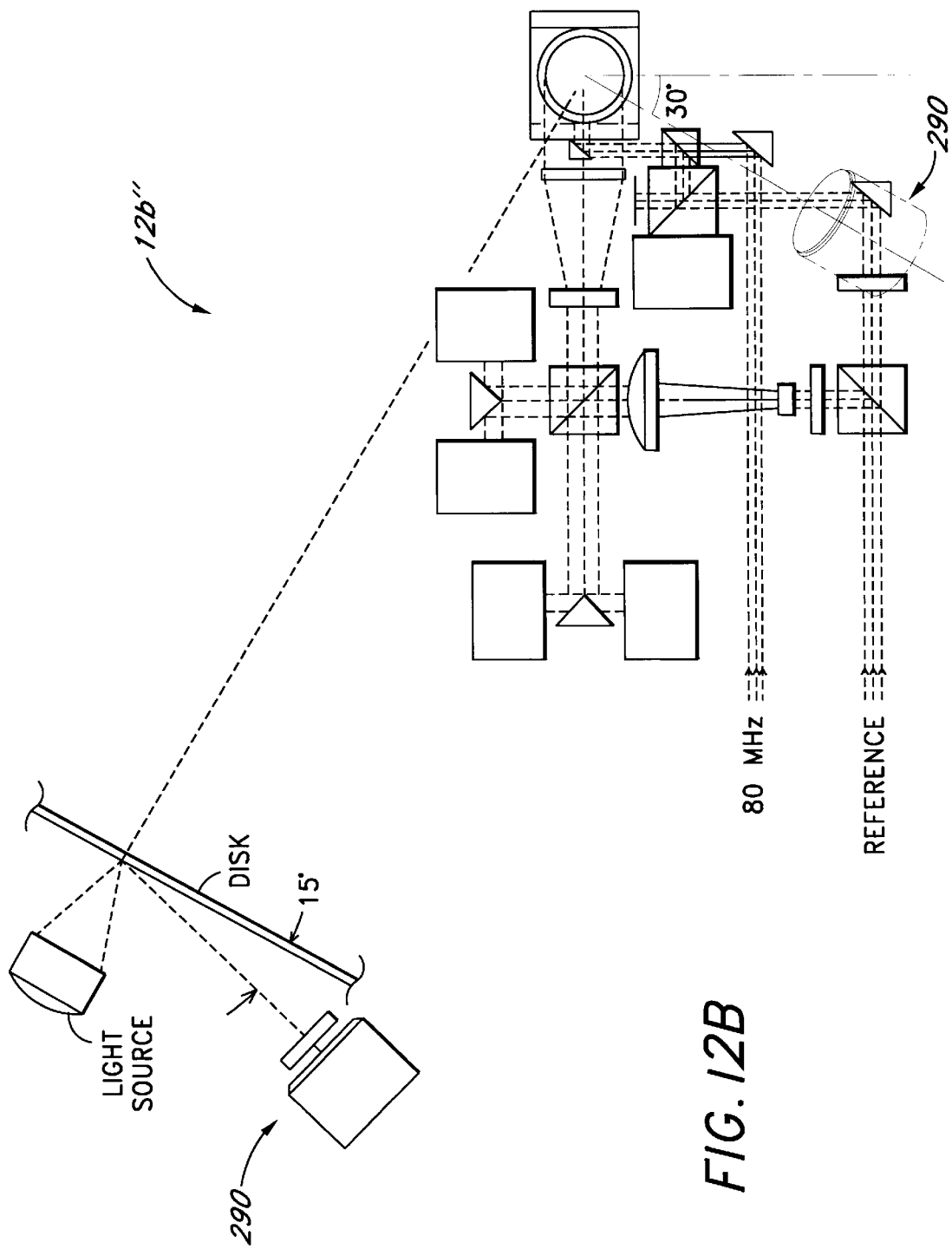
FIG. 12B illustrates a further embodiment of the sensor interferometer module 12b as shown in FIG. 5.

FIG. 12B illustrates yet another embodiment of the sensor interferometer module 12b as shown in FIG. 5. The sensor interferometer module 12b" is shown in two views, and may be implemented using the sensor interferometer module 12b of FIG. 5 or 12b' of FIG. 12 with the addition of a particle discrimination channel 290. The implementation of the particle discrimination channel 290 is described in detail in pending U.S. patent application Ser. No. 08/588,870 entitled "Surface Inspection Apparatus and Method" which is assigned to the assignee of the present invention and incorporated herein by reference.

The particle discrimination channel 290 may be implemented in the apparatus of the present invention as a way of providing particle discrimination. Particles tend to scatter light at very large angles from the illumination angle-of-incidence. By threshold detecting electrical pulses which are produced by this highly scattered light, disk surface asperities may be fairly reliably classified as particles and not bumps. This particle discrimination channel 290 consists of a collimating lens (plano-convex), a linear polarizer, and a photomultiplier tube. The focused illumination spot on the disk surface would be nominally located at the front focal point of the collimating lens. The computer-based signal processing algorithms are used to classify the asperities.

A further aspect of the present invention includes the frequency demodulator 64 of FIG. 6. The demodulator 64 can demodulate FM signals with very large frequency deviations and very high modulation rates. This is accomplished without requiring a low-pass filter with a steep response, which is both costly and which provides undesirable phase characteristics. While conventional FM demodulators which detect the zero-crossings of the input signal rely on one or two zero-crossings per cycle, the demodulator 300 of the present invention creates a larger number of zero-crossings per cycle. This results in a higher zero-crossing frequency, which is significantly higher than the modulation frequency, and therefore much simpler to filter. The low-pass filter utilized by the demodulated 300 of the present invention can thus have a more gradual roll-off and will therefore have significantly reduced group delay variation in the pass-band.

The demodulator 64 of the present invention first increases the number of zero-crossings per cycle. These zero-crossings are each used to trigger a pulse generator which produces a precise pulse having accurate amplitude and duration for each zero-crossing. These pulses are then summed by a linear summing network, and then fed into a low-pass filter which outputs a voltage that is proportional to the frequency of the zero crossings. The output voltage thus obtained thereby accurately represents the modulation signal.

Figure 13A:
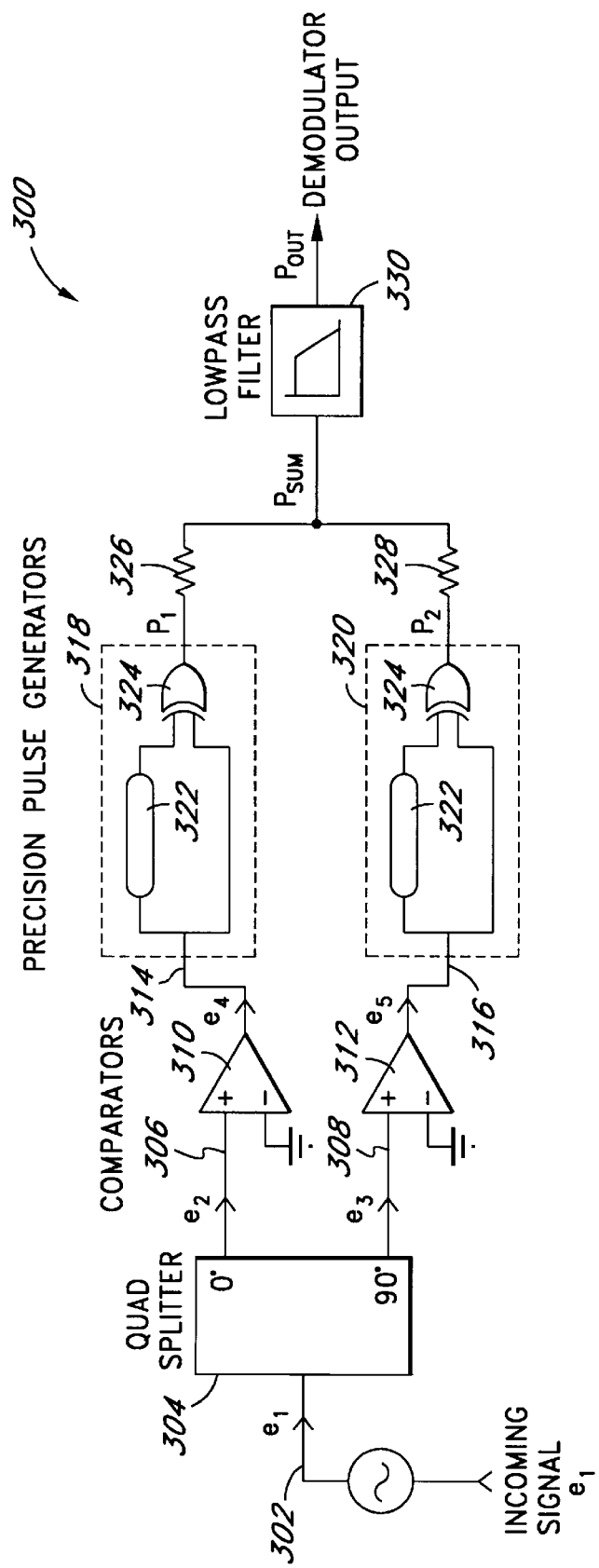
FIG. 13A illustrates one embodiment of the demodulator 300 of the present invention.
Figure 13B:
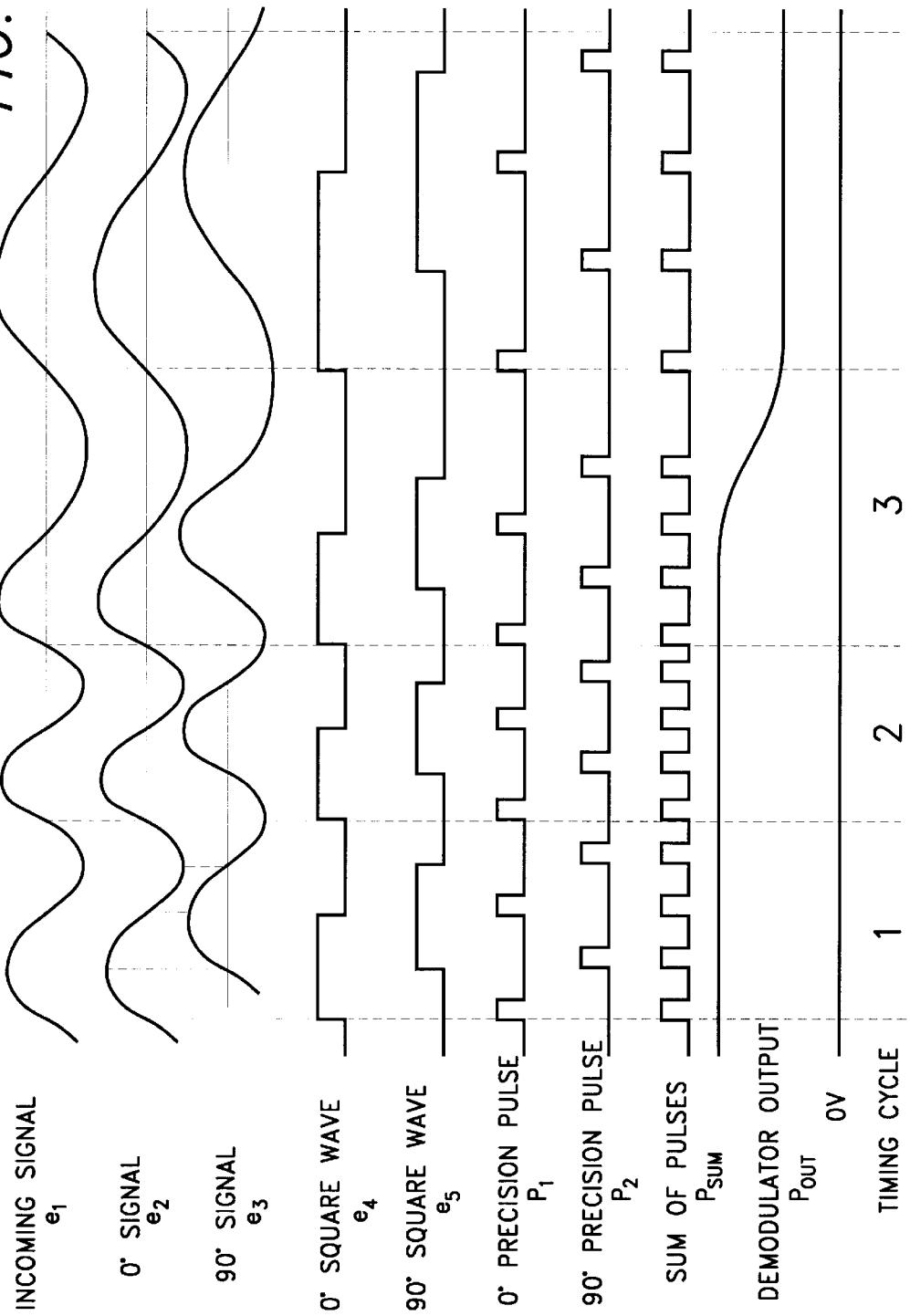
FIG. 13B illustrates the timing cycles of the signals received and generated by the demodulator 300 of FIG. 13A.

One embodiment of the demodulator 64 includes the demodulator 300 as shown in FIG. 13A. FIG. 13B illustrates the timing cycles of the signals received and generated by the demodulator 300. As shown, the incoming signal $e_1$ is passed via signal line 302 through a quadrature splitter 304. The quadrature splitter 304 generates two signals $e_2$ and $e_3$ which are representative of the incoming signal $e_1$, as shifted by 0 and 90 degrees, respectively. Each of these signals $e_2$ and $e_3$ are provided via signal lines 306 and 308 to digital comparators 310 and 312, which generate two square wave signals $e_4$ and $e_5$ in response. The square wave signals $e_4$ and $e_5$ are approximately 90 degrees apart in phase from each other. Since each of these waves $e_4$ and $e_5$ has two zero-crossings per timing cycle (see FIG. 13B), and since they are 90 degrees out of phase with each other, the result is that the demodulator 300 has effectively generated four zero-crossings per cycle.

The output signals $e_4$ and $e_5$ of the comparators 310 and 312 are next provided to precision pulse generators 318 and 320, respectively, which generate precise pulses $P_1$ and $P_2$, respectively. Each generator 318 and 320 includes a delay line 322 and an exclusive-OR gate 324. One precise pulse $P_1$ or $P_2$ is generated per zero-crossing and these pulses $P_1$ and $P_2$ are summed together via resistors 326 and 328. The sum of the precise pulses, $P_{sum}$, is filtered via a low-pass filter 330 to provide output signal $P_{out}$.

FIG. 13B illustrates the incoming signal, $e_1$, the two quadrature signals $e_2$ and $e_3$, the square waves $e_4$ and $e_5$, the precision zero-crossing pulses $P_1$ and $P_2$, the sum $P_{sum}$ of these pulses and the low-pass filter output $P_{out}$. Since four pulses are generated per timing cycle (instead of one or two with a conventional detector), the frequency of zero-crossings is twice or four times as high as compared to a conventional detector. Hence, a low-pass filter 330 with a higher cut-off frequency may be used, and consequently larger frequency deviations can be demodulated at higher modulation rates. Demodulator 300 therefore responds more rapidly to frequency changes in the incoming signal $e_1$.

It will be apparent to those skilled in the art that the method of the preferred embodiment may be improved further by using a four-way splitter having 0, 45, 90 and 135 degree outputs. Each of these outputs could be fed to a comparator, zero-crossing detector and precision pulse generator similar to that described above. The outputs of these four pulse generators would be summed by a four way resistive summer, resulting in eight zero-crossings per cycle. This would result in a demodulator that is further improved in speed of response, and is now twice as fast as before, and four or eight times faster than a conventional zero-crossing demodulator.

Figure 14A:
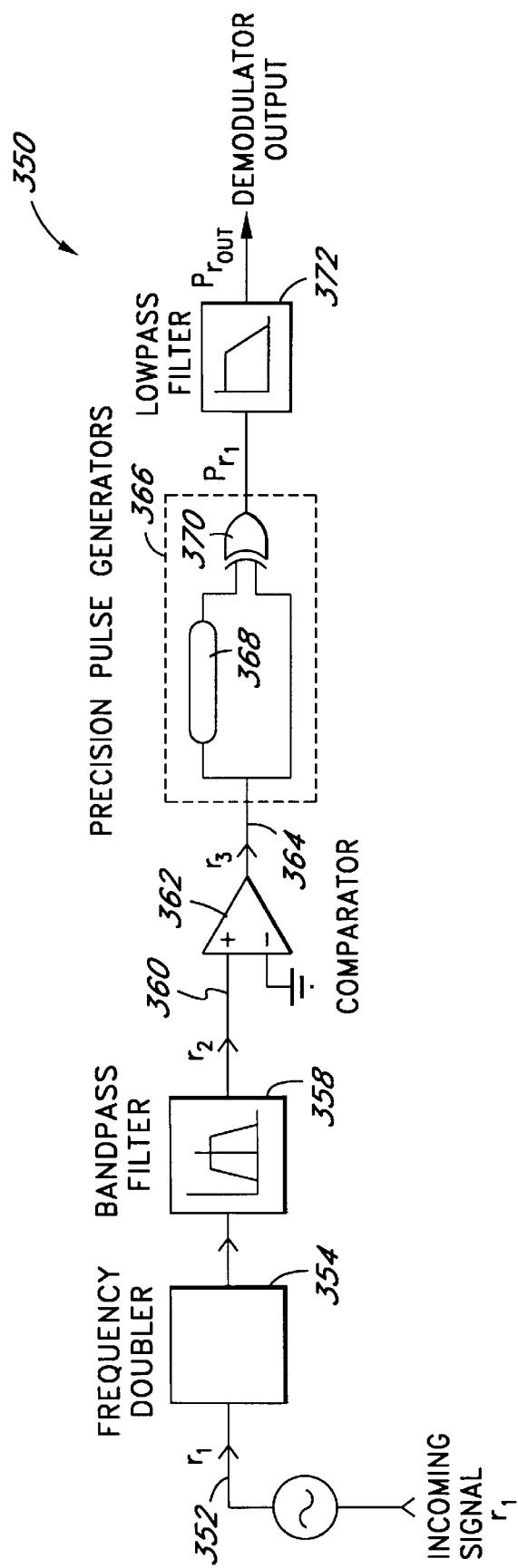
FIG. 14A illustrates a second embodiment of the demodulator 350 of the present invention.

FIG. 14A illustrates a second embodiment 350 of the frequency demodulator 64 of FIG. 6. In this embodiment 350, the incoming signal $r_1$, is passed via line 352 through a frequency doubler 354 and a band-pass filter 358 having a center frequency at twice the center frequency of the input signal $r_1$. The frequency doubler 354 in combination with the bandpass filter 358 generate a signal $r_2$ with twice the frequency of the incoming signal $r_1$. This signal $r_2$ is then provided via signal line 360, to a digital comparator 362 which generates a square wave signal $r_3$ that has twice the frequency of the input signal $r_1$ and four times as many zero crossing per cycle. A precise pulse is $P_{r_1}$ is generated by precise pulse generator 366. The precise pulse generator 366 includes a delay line 368 and exclusive-OR gate 370. The pulses $P_{r_1}$ are then filtered via a low-pass filter 372 to provide an output signal $P_{rout}$.

Figure 14B:
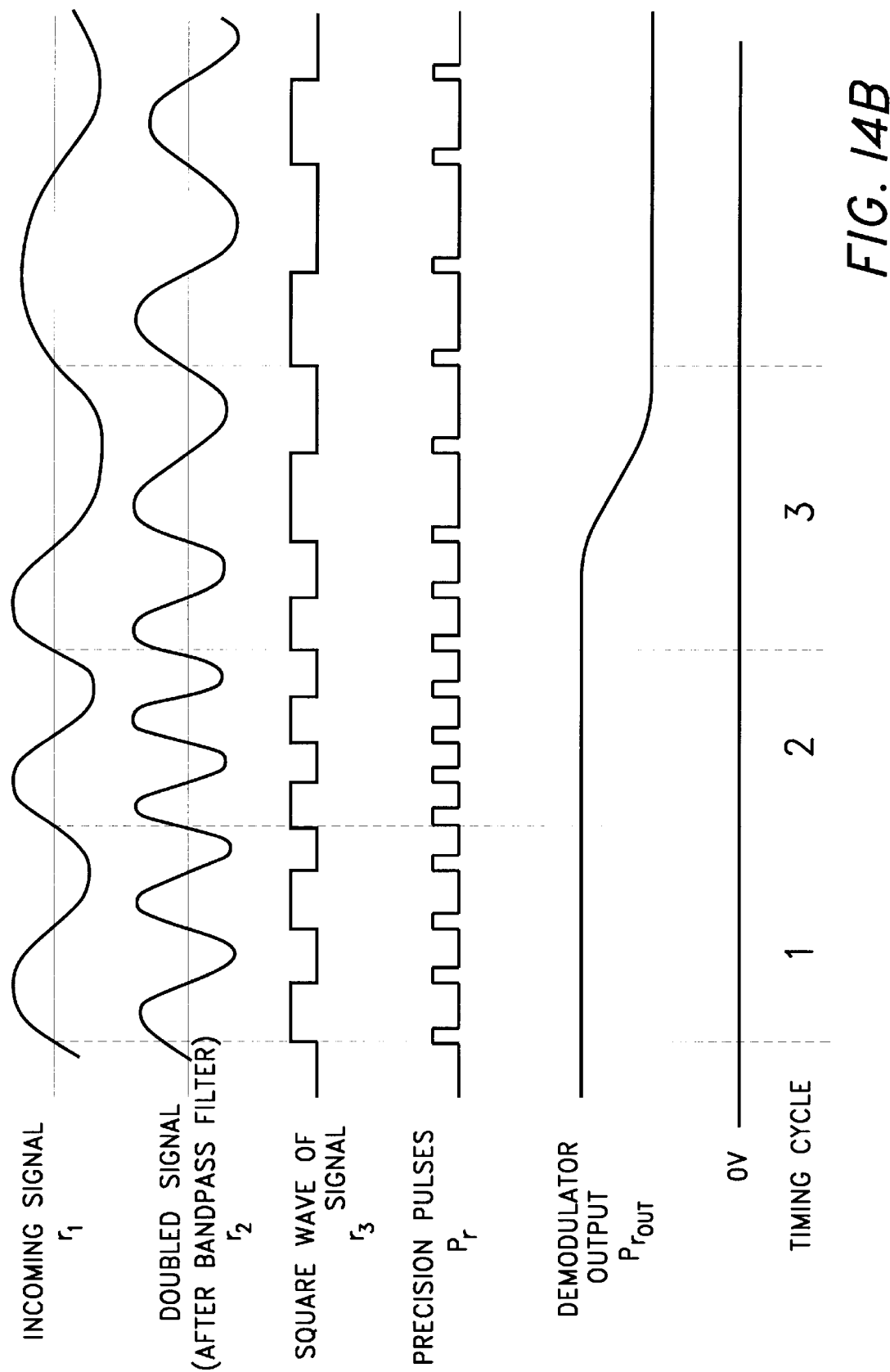
FIG. 14B illustrates the timing cycles of the signals received and generated by the demodulator 350 of FIG. 14A.

FIG. 14B illustrates the timing cycles of the signals received and generated by demodulator 350. Since four pulses are generated per cycle (instead of 1 or two with a conventional detector), as with the first embodiment 300 described above, demodulator 350 has an output $P_{rout}$ that responds more rapidly to frequency changes in the incoming signal $r_1$.

Figure 15A:
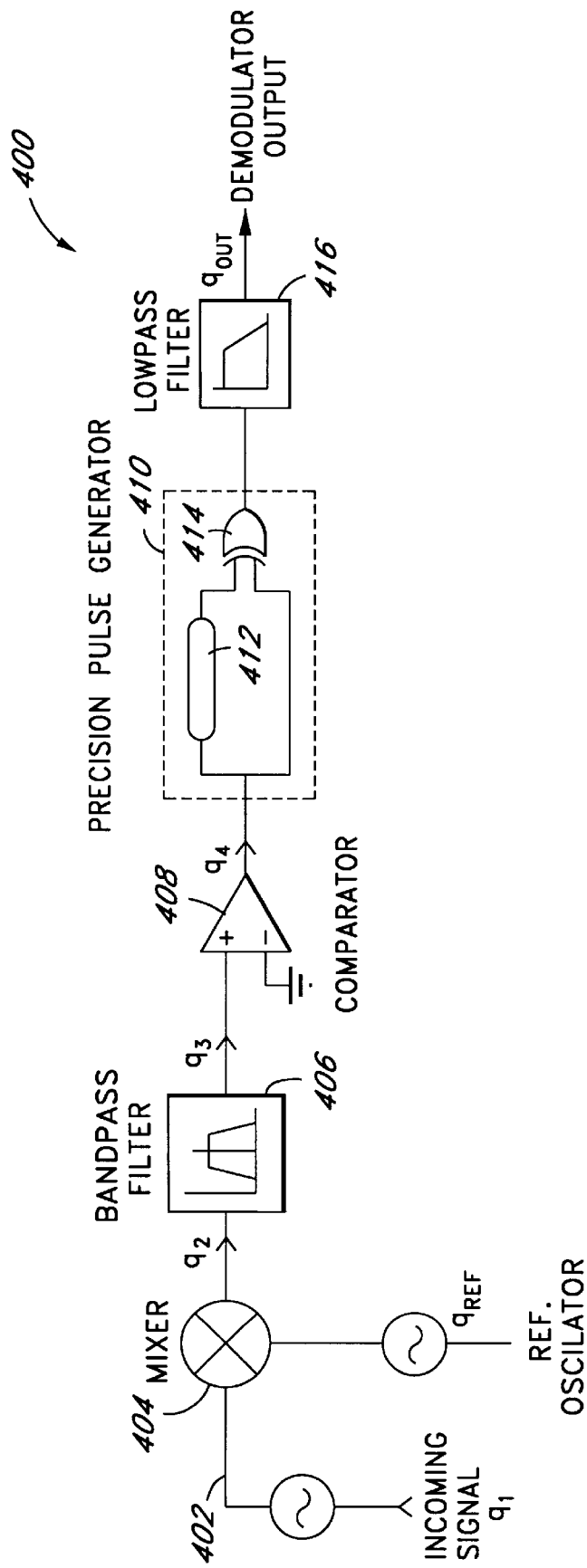
FIG. 15A illustrates a third embodiment of the demodulator 400 of the present invention.
Figure 15B:
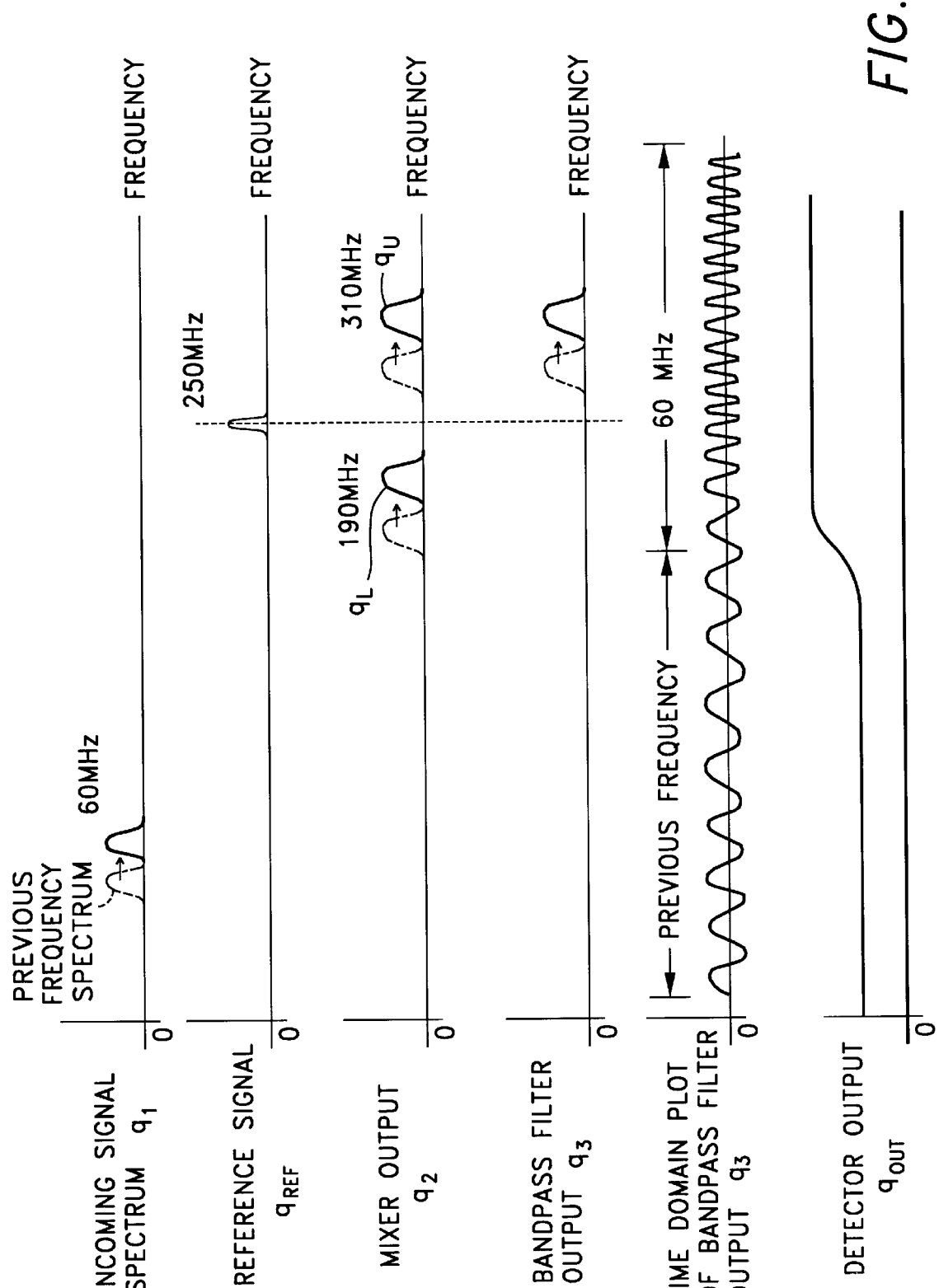
FIG. 15B illustrates the timing cycles of the signals received and generated by the demodulator 400 of FIG. 15A.

FIG. 15A illustrates a third alternate embodiment 400 of the frequency demodulator 64. FIG. 15B illustrates the timing cycles of the signals received and generated by the demodulator 64. Referring to both FIGS. 15A and 15B, the incoming signal $q_1$ is passed via signal 402 though a frequency mixer 404. The frequency mixer 404 mixes the incoming signal $q_1$ with a reference signal $q_{ref}$ to provide an output $q_2$ having two sidebands. The lower sideband signal $q_1$ spectrum (see FIG. 15B) is centered at a frequency that is the difference between those of the incoming signal $q_1$ and the reference signal $q_{ref}$. The upper sideband signal $q_u$ spectrum is centered at a frequency that is the sum of those of the incoming signal $q_1$ and the reference signal $q_{ref}$.

Hence, if the input frequency is at 60 MHz and the reference is at 250 MHz, the upper sideband signal $q_u$ is at 310 MHz. The mixer output $q_2$ is provided to a band-pass filter 406, which passes the upper sideband signal $q_u$ but blocks the lower sideband signal $q_L$. The output $q_3$ of the filter contains only the signal $q_u$, which in this example is the 310 MHz frequency. In the present example, $q_u$ is over five times the input frequency. This signal $q_u$ (or $q_3$) is provided to a comparator 408, and then to a precision pulse generator 410 which has a delay line 412 and exclusive-OR gate 414. The signal $q_3$ is filtered via a low-pass filter 416, whose output voltage $q_{out}$ is proportional to the frequency of the incoming signal $q_1$. Since over ten pulses are generated per cycle (instead of one or two with a conventional detector), the demodulator 400 provides an output that responds more rapidly to frequency changes in the incoming signal $q_1$.

The demodulators 300, 350 and 400 of the present invention can accommodate high modulation frequencies while blocking undesirable signal energy at the zero-crossing frequency of the modulated signal. In addition, the demodulators 300, 350 or 400 exhibit minimal phase and group delay variations in the pass-band. Because the pulse train has a frequency that is greater than the input frequency, the ripple on the filtered output is reduced. Thus, a low-pass filter with a more gradual roll-off and a higher cut-off frequency can be used, which provides a more linear group delay and a faster response, respectively.

The advantages provided by the heterodyne interferometer of the present invention includes the use of the darkfield channel in an interferometric mode to measure the height or depth of defects on a magnetic disk surface which are substantially smaller in diameter than the illumination spot. The high lateral sensitivity provided by collecting light in the darkfield channels is therefore combined with the high axial sensitivity provided by the use of an interferometric approach. The use of a darkfield channel provides high lateral sensitivity even with a large illumination spot. Defects with lateral dimensions of less than a micron can be reliably detected with illumination spots as large as 10–20 μm in diameter. The heterodyne interferometer of the present invention also provides excellent height sensitivity and preserves polarity to permit bump/pit discrimination.

In the heterodyne interferometer of the present invention, a large illumination spot may be used, which not only permits high throughput, due to a large track pitch, but which also provides a large depth-of-focus which eliminates the need for a complex focus servo. This in turn permits spinning the disk at very large angular velocities, such as 10,000–15,000 r.p.m. with conventional air bearing spindles.

There are numerous other embodiments of the heterodyne interferometer of the present invention which will be obvious to one skilled in the art, including but not limited to changes in the dimensions of the optical path, the type of optical elements, the location and type of detectors, the number of detectors and optical elements, etc. Additionally, it will be understood that the apparatus and method of the present invention for sampling defects in a medium may be employed with any plate-shaped medium including compact disks or plate-shaped metal surfaces which require finishing to extremely close tolerances.

The apparatus and method of the present invention may be embodied in other specific runs without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for detecting defects on a disk surface, comprising:
    a light source that generates a beam of light;
    a beamsplitter for splitting light emanating from the light source into a first portion and a second portion;
    a modulator for modulating the second portion of light into a modulated beam for illuminating the surface, wherein the modulated light beam is reflected from the surface, the modulated beam reflected from the surface including nonspecularly reflected light and specularly reflected light, the specularly reflected light interfering with the first portion of the light to provide a first interference signal;
    a first detector for receiving the first interference signal, the first detector generating a first output signal representative of a profile of the defect in response to the first interference signal; and
    a second detector for receiving the nonspecularly reflected light and the first portion of the light, the nonspecularly reflected light and the first portion of the light interfering to provide a second output signal representative of a profile of the defect.

2. The apparatus of claim 1 further comprising:
    a reflector located such that substantially all specularly reflected light circumvents the reflector.

3. The apparatus of claim 1 further comprising a demodulator coupled to the first detector, the demodulator for demodulating the output of the first detector to provide the first output signal.

4. The apparatus of claim 3, wherein the demodulator comprises:
    a circuit for receiving a frequency modulated signal, the circuit providing an output signal having a frequency that is greater than that of the received signal;
    a precision pulse generator coupled to the circuit for generating a pulse representative of the frequency of the output signal; and
    a filter coupled to the precision pulse generator for filtering the pulse.

5. The apparatus of claim 4, wherein the circuit comprises a frequency doubling circuit and a comparator.

6. The apparatus of claim 4, wherein the circuit comprises:
    a frequency mixer for mixing the received signal with a reference signal, the frequency mixer providing an output signal having an upper sideband and a lower sideband;
    a filter which filtering the lower sideband; and
    a comparator coupled to the filter.

7. The apparatus of claim 1, wherein the profile of the defect includes information used to compute the surface acceleration of the defect.

8. The apparatus of claim 1, wherein the profile of the defect includes the height of the defect.

9. An apparatus for detecting defects on a disk surface comprising:
    a light source that generates a beam of light;
    a first beamsplitter for splitting the light emanating from the light source into a first portion and a second portion;
    a modulator for modulating the second portion of light into a modulated beam for illuminating the surface wherein the modulated light beam is nonspecularly reflected from the surface, and wherein the nonspecularly reflected light includes forward scattered light and back scattered light;
    a second beamsplitter for splitting the nonspecularly reflected light into a first beam and a second beam, the first beam including a first forward scattered light beam and a first back scattered light beam, the second beam including a second forward scattered light beam and a second back scattered light beam;
    a first prism for receiving the first forward scattered light beam and the first back scattered light beam;
    a second prism for receiving the second forward scattered light beam and the second back scattered light beam;
    a first detector and a second detector for respectively receiving the first forward scattered light beam and the first back scattered light beam;
    a third detector and a fourth detector for respectively receiving the second forward scattered light beam and the second back scattered light beam;
    a first differential amplifier having a first terminal for receiving an output from the first detector, and a second terminal for receiving an output from the third detector, the first differential amplifier providing an output representative of a profile of the defect based on the forward scattered light; and
    a second differential amplifier having a first terminal for receiving an output from the second detector, and a second terminal for receiving an output from the fourth detector, the second differential amplifier generating an output representative of a profile of the defect based on the back scattered light.

10. The apparatus of claim 9, wherein said nonspecular surface reflection is reflected off a nonspecular region of the surface, said nonspecular region including upward-sloping regions and downward-sloping regions.

11. The apparatus of claim 10, further comprising a signal processor configured to receive the first output signal, the signal processor identifying points on the surface at which upward-sloping regions on the surface are adjacent to downward-sloping regions on the surface, said signal processor also determining the order in which the two regions are detected.

12. The apparatus of claim 11, wherein the signal processor issues a first processor output signal indicative of a bump when an upward-sloping region is detected before an adjacent downward sloping region, said signal processor issuing a second processor output signal indicative of a pit when a downward-sloping region is detected before an adjacent upward-sloping region.

13. The apparatus of claim 12, wherein said first processor output signal is issued when the output of the first differential amplifier is received before the output of the second differential amplifier is received.

14. The apparatus of claim 12, wherein said second processor output signal is issued when the output of the second differential amplifier is received before the output of the first differential amplifier is received.

15. A method for detecting defects on a surface, comprising the steps of:

splitting light emanating from the light source into a first portion and a second portion;

modulating the second portion of light into a modulated beam for illuminating the surface;

reflecting the second portion of light from the surface, the reflected light including specularly reflected light and nonspecularly reflected light;

interfering the specularly reflected light with the first portion of the light to provide a first output signal representative of a profile of the defect and interfering nonspecularly reflected light reflected from the surface with the first portion of the light to provide a second output signal representative of a profile of the defect.

16. The method of claim 15, further comprising the step of demodulating the output of the detector to provide the first output signal.

17. The method of claim 15, further comprising the steps of:

splitting the nonspecularly reflected light into a first beam and a second beam, the first beam including a first forward scattered light beam and a first back scattered light beam, the second beam including a second forward scattered light beam and a second back scattered light beam;

generating a second output signal representative of a profile of the defect based on the forward scattered light; and generating a third output signal representative of a profile of the defect based on the back scattered light.

18. The method of claim 17, wherein the profile of the defect includes information used to compute the surface acceleration of the defect.

19. The method of claim 17, wherein in the steps of generating the second and third output signals, the profile of the defect includes the height of the defect.

20. The method of claim 17, wherein a nonspecular surface reflection is reflected off a nonspecular region of the surface, said nonspecular region including upward-sloping regions and downward-sloping regions.

21. The method of claim 18, further comprising the steps of identifying points on the surface at which upward-sloping regions on the surface are adjacent to downward-sloping regions on the surface, and determining the order in which the two regions are detected.

22. The method of claim 21, further comprising the steps of issuing a first surface output signal indicative of a bump when an upward-sloping region is detected before an adjacent downward sloping region, and issuing a second surface output signal indicative of a pit when a downward-sloping region is detected before an adjacent upward-sloping region.

23. The method of claim 22, wherein said first surface output signal is issued when the second output signal is generated before the third output signal is generated.

24. The method of claim 22, wherein said second surface output signal is issued when the output third output signal is generated before the second output signal is generated.

* * * * *